(12) United States Patent
Livneh et al.

(10) Patent No.: US 10,033,106 B2
(45) Date of Patent: Jul. 24, 2018

(54) TRANSDERMAL ANTENNA

(75) Inventors: Noam Livneh, Yuvalim (IL); Yoav Mintz, Jerusalem (IL); Vered Bar-Bracha, Hod Hasharon (IL); Arik Bracha, Hod Hasharon (IL)

(73) Assignee: Hadasit Medical Research Services & Development Ltd., Jerusalem (IL)

( * ) Notice: Subject to any disclaimer, the term of this patent is extended or adjusted under 35 U.S.C. 154(b) by 1162 days.

(21) Appl. No.: 13/499,913

(22) PCT Filed: Oct. 3, 2010

(86) PCT No.: PCT/IL2010/000793
§ 371 (c)(1),
(2), (4) Date: Apr. 3, 2012

(87) PCT Pub. No.: WO2011/039752
PCT Pub. Date: Apr. 7, 2011

(65) Prior Publication Data
US 2012/0203082 A1    Aug. 9, 2012

Related U.S. Application Data

(60) Provisional application No. 61/248,421, filed on Oct. 3, 2009.

(51) Int. Cl.
*A61B 5/07*    (2006.01)
*H01Q 9/30*    (2006.01)
(Continued)

(52) U.S. Cl.
CPC .......... *H01Q 9/30* (2013.01); *A61B 1/00016* (2013.01); *A61B 17/00234* (2013.01);
(Continued)

(58) Field of Classification Search
CPC .................................................. A61B 5/073
See application file for complete search history.

(56) References Cited

U.S. PATENT DOCUMENTS 3,612,050 A * 10/1971 Sheridan ........... A61M 25/0606
604/166.01
4,498,902 A * 2/1985 Ash et al. ................. 604/164.05
(Continued)

FOREIGN PATENT DOCUMENTS

CN    101322639    12/2008
CN    101534738    9/2009
(Continued)

OTHER PUBLICATIONS

"A Review of IR Transmitting, Hollow Waveguides" by Harrington, Fiber and Integrated Optics, vol. 19, pp. 211-217, 2000.*
(Continued)

*Primary Examiner* — Tiffany Weston
(74) *Attorney, Agent, or Firm* — A.C. Entis-IP Ltd.

(57) ABSTRACT

A transdermal antenna may be partially inserted into a cavity in the body of a mammal to receive wireless data transmissions from devices located within the body and relay the data to devices located outside of the body. The transdermal antenna may include a first antenna which may be inserted inside of the body cavity and receive radio frequency data transmissions from devices located inside the body. The transdermal antenna may conduct the received data transmissions to a relay mechanism located outside of the body using coaxial cables, waveguides or a combination of both. The relay mechanism may relay the conducted data transmissions to a receiver device located outside of the body by using a wire connection, such as a coaxial cable, or a wireless communication link via a transceiver coupled to a second antenna.

11 Claims, 24 Drawing Sheets

(51) Int. Cl.
  *A61B 1/00* (2006.01)
  *A61B 17/00* (2006.01)
  *H01Q 1/27* (2006.01)
  *A61B 90/00* (2016.01)
  *A61B 1/313* (2006.01)
  *A61B 5/00* (2006.01)
  *A61B 34/30* (2016.01)

(52) U.S. Cl.
  CPC ............ *A61B 90/361* (2016.02); *A61B 90/37* (2016.02); *H01Q 1/273* (2013.01); *A61B 1/313* (2013.01); *A61B 5/0013* (2013.01); *A61B 2017/00221* (2013.01); *A61B 2034/302* (2016.02)

(56) References Cited

U.S. PATENT DOCUMENTS

| | | | |
|---|---|---|---|
| 6,408,202 | B1 | 6/2002 | Lima et al. |
| 6,428,470 | B1* | 8/2002 | Thompson ......... A61B 1/00096 600/114 |
| 6,626,902 | B1* | 9/2003 | Kucharczyk et al. ......... 606/41 |
| 8,790,245 | B2 | 7/2014 | Fernandez et al. |
| 9,339,285 | B2 | 5/2016 | Rodriguez-Navarro et al. |
| 9,610,133 | B2 | 4/2017 | Ma et al. |
| 2003/0199755 | A1* | 10/2003 | Halperin et al. ............. 600/411 |
| 2008/0309758 | A1 | 12/2008 | Karasawa et al. |
| 2010/0042010 | A1* | 2/2010 | Dekker ............... A61B 5/0031 600/523 |
| 2011/0077697 | A1* | 3/2011 | Rofougaran ......... G06F 19/323 607/2 |
| 2012/0089207 | A1* | 4/2012 | Chen ................... A61N 5/0601 607/92 |
| 2014/0276941 | A1 | 9/2014 | Rodriguez-Navarro et al. |
| 2016/0302811 | A1 | 10/2016 | Rodriguez-Navarro et al. |

FOREIGN PATENT DOCUMENTS

| | | |
|---|---|---|
| EP | 1186274 | 3/2002 |
| JP | 06-070906 | 3/1994 |
| JP | 2002514111 | 5/2002 |
| JP | 2009072368 | 4/2009 |
| WO | 2008044000 | 4/2008 |
| WO | 2016168377 | 10/2016 |
| WO | 2016168380 | 10/2016 |
| WO | 2017120540 | 7/2017 |

OTHER PUBLICATIONS

European Examination Report, 10775910.2 dated Oct. 8, 2013.
International Search Report; PCT/IL2010/000793; dated Apr. 21, 2011.
Office Action dated Jun. 1, 2014 for corresponding Israeli Application No. 218982.
Office Action dated May 27, 2014 for corresponding Japanese Application No. 2012 531552.
Office Action dated Jun. 5, 2014 for corresponding Chinese Application No. 2010800548745.
Office Action dated Oct. 6, 2016 for corresponding European Application No. 10775910.2 filed Apr. 27, 2012.
Office Action dated May 27, 2015 for corresponding Japanese application No. 2012-531552.

\* cited by examiner

TRANSDERMAL ANTENNA

RELATED APPLICATIONS

The present application is a US National Phase of PCT Application No. PCT/IL2010/000793, filed on Oct. 3, 2010, which claims benefit under 35 U.S.C. § 119(e) of U.S. Provisional Application 61/248,421 filed on Oct. 3, 2009, the disclosure of which is incorporated herein by reference.

FIELD OF THE INVENTION

The present invention relates generally to antennas and more particularly, to transdermal antennas capable of relaying data and control communications between devices inside of a patient's body cavity and devices outside of the body.

BACKGROUND

The number of laparoscopic surgeries that are performed is on the rise. In performing laparoscopic surgeries, surgeons make smaller skin incisions and use special instruments and techniques which in some cases can reduce blood loss, expedite post operative recovery and reduce post operative pain. Therefore, when possible, patients and their surgeons prefer laparoscopic surgeries over open surgeries.

The success of laparoscopic surgeries depends on sophisticated video-camera technology, precise surgical instruments and experienced surgeons. During a laparoscopic surgery, cameras act as a surgeon's eyes and instruments as their hands and fingers. Therefore, technological advances in the equipment used during laparoscopic surgeries may lead to more successful surgeries and better post operative prognosis. However, a mammalian body presents a unique environment which can limit the use of certain technologies. For example, equipments that employ wire connections for data transmission limit the surgeons' capability to operate freely within the body cavity due to restriction of movements by the cables. Also, wireless technologies that use high frequency signals may be limited, because high frequency signals are absorbed by tissues limiting or precluding transmission of data through the body.

SUMMARY

A transdermal antenna of the various embodiments enables data and control communications between devices located inside of a patient's body and a receiver or controller device located outside of the body. In the various embodiments, the transdermal antenna may include a shaft, a first antenna located at a first end of the shaft and a second antenna or transceiver located at a second end of the shaft. The first end of the transdermal antenna may be inserted into a mammalian body so the first antenna can receive data transmissions from devices located within the body. The radio frequency signals received by the first antenna may be conducted through the shaft to the second via a coaxial cable, a waveguide or a combination of a coaxial cable and a waveguide. At the second end, the radio frequency signals may be conducted to an external receiver device via a cable, such as a coaxial cable, or received and retransmitted by a transceiver for reception by an external receiver device.

BRIEF DESCRIPTION OF THE DRAWINGS

The accompanying drawings, which are incorporated herein and constitute part of this specification, illustrate exemplary embodiments of the invention, and together with the general description given above and the detailed description given below, serve to explain the features of the invention.

DETAILED DESCRIPTION

Figure 1:
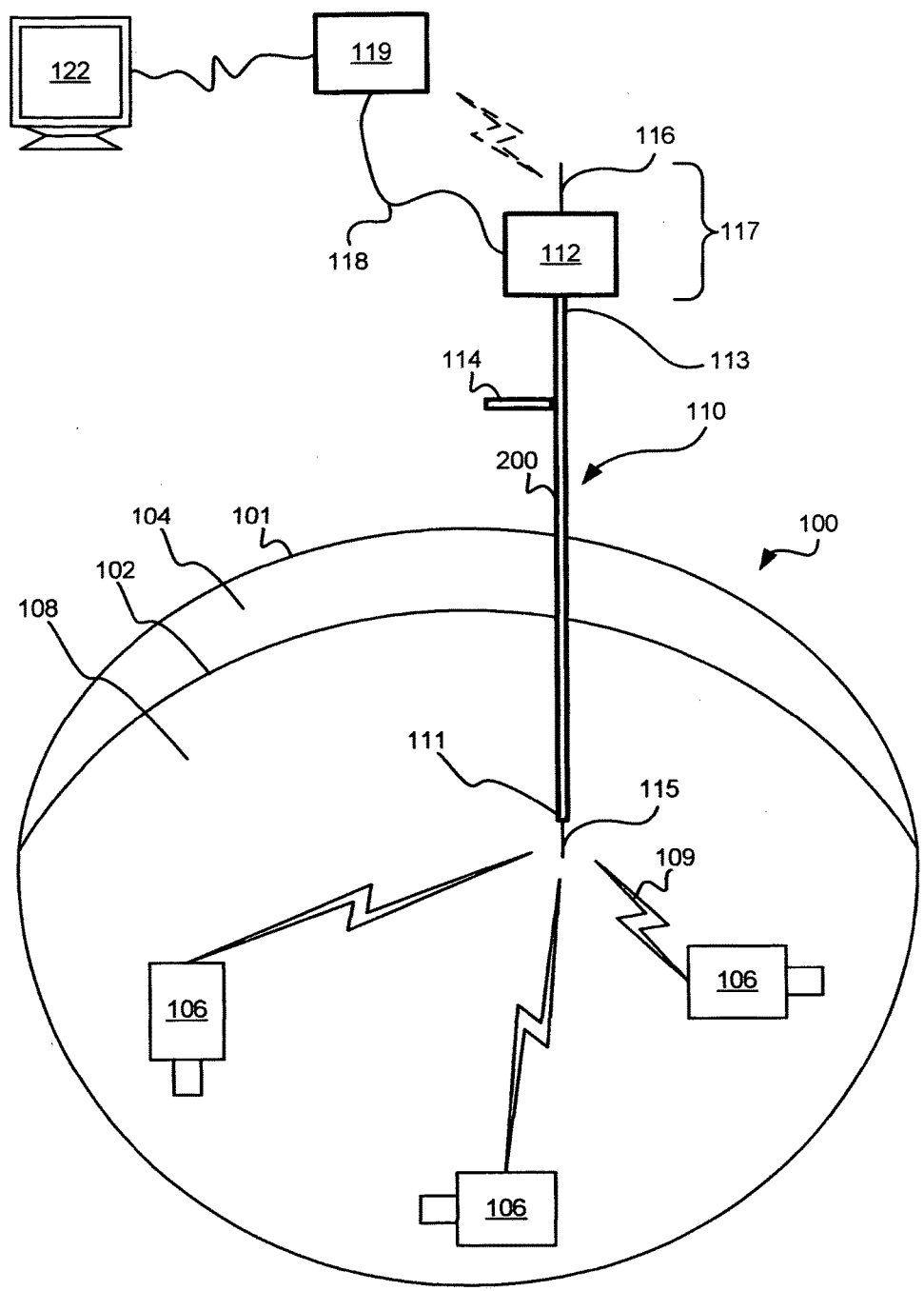
FIG. 1 is a system component diagram according to the various embodiments.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

The word "exemplary" is used herein to mean "serving as an example, instance, or illustration." Any implementation described herein as "exemplary" is not necessarily to be construed as preferred or advantageous over other implementations.

During a laparoscopic surgery, cameras act as surgeons' eyes and instruments as their hands and fingers. Therefore, the success of laparoscopic surgeries depends on sophisticated video-camera technology, precise surgical instruments and experienced surgeons. Advances in technology provide surgeons with more sophisticated and precise instruments which in turn can improve the overall quality of surgical operations. For example, advanced camera systems can be developed to provide high quality high definition images to surgeons during the surgery. Data transmission from these high definition cameras, however, depends on the use of cables or wireless transmissions to deliver the image data to an external receiver device which can present the images to the surgeon.

Current high-definition video cameras used in minimally invasive surgery today are connected to a receiver device outside the body via cables. Each camera view is limited and each camera requires a dedicated trocar or robot arm. This can be very limiting for surgeons. To overcome such limitations, surgeons are envisioning the cable free HDTV camera that can be placed anywhere within the cavity inflated for the surgery.

Due to the inconvenience and the limitations imposed by wires on moving tools without hitting the wires and moving the camera inadvertently, connecting TV cameras to external receivers by cables is disfavored for many reasons. Also, cables connecting a high performance device located within a body cavity to outside devices may pose a safety risk, particularly in electrical fault conditions, because the cables can be a source of electric shock to patients. Therefore, it is envisioned that wireless cameras will be developed to transmit data to a receiving device located outside of the body.

The use of wireless technology, such as wireless high definition cameras, to transmit data from inside of the body to receiving devices located outside of the body is limited. High definition cameras require the use of high bandwidths to carry high definition television data. However, body tissues absorb high-bandwidth transmissions. Wireless data links that use signals centered on a much lower carrier frequency which are capable of penetrating body tissues are also not useful, because the low bandwidth of such signals can not carry high definition television data.

To enable transmission of high capacity data signals through body tissues, the various embodiments provide an antenna that conducts radio frequency signals through the dermal and subcutaneous layers of a body, which is referred to herein as a "transdermal antenna." The transdermal antenna can be partially inserted into a body cavity to receive wireless data transmissions from devices positioned inside of the body, conduct the data transmissions across a body tissue boundary, and relay the data transmissions to receiver devices located outside of the body.

The word "relay" is used herein to refer generally to a mechanism by which radio frequency signals received by the transdermal antenna are transmitted on to an external receiver device. As described in the various embodiments, radio frequency signals received by the transdermal antenna may be relayed by: "conduction" through a cable (e.g., a coaxial cable) connected to the external receiver device; by "retransmission" via a transceiver that receives signals from the transdermal antenna and wirelessly transmits the signals from an external antenna for reception by the external receiver device; or by "re-radiation" from an external antenna for reception by the external receiver device without the benefit of a transceiver amplifying or reformatting the signal. For ease of reference, a mechanism that relays radio frequency signals received by the transdermal antenna to an external receiver device is referred to herein generally as a "relay mechanism." As described in the various embodiments, a relay mechanism may include a transceiver, a cable, a connection to a cable, an external antenna, and combinations thereof.

The transdermal antenna of the various embodiments may take advantage of the low loss propagation of wireless signals within an inflated body cavity created for laparoscopic surgery. For example wireless cameras may be inserted into the body using a trocar or NOTES robot arm. The transdermal antenna may be partially inserted into the body cavity so that a first end is positioned within the inflated cavity and the second end is positioned outside the body. For ease of reference, the first end may also be referred to as the "internal end" or "proximal end" (i.e., proximal to the patient) and the second end may be referred to as the "external end" or "distal end" consistent with the intended use of the transdermal antenna. The portion inside the cavity may include a first antenna that can receive data transmissions from the inserted cameras. The first (inner) antenna is connected to a coaxial cable or a waveguide that conducts the received data transmissions to the second end where a relay mechanism relays the data transmissions to a receiver device outside of the body with low loss of signal strength. In a first embodiment, the relay mechanism may be a cable or cable connection so that the data transmissions are conducted from the second end of the transdermal antenna to the receiver device by a cable or waveguide that is coupled to the transdermal antenna. This embodiment may include a cable connection on the second end of the transdermal antenna and optionally a relay circuit that facilitates coupling the data transmissions to the cable or waveguide. In a second embodiment, the relay mechanism may be a wireless transceiver so that the data transmissions are re-transmitted wirelessly by the transceiver coupled to the second end of the transdermal antenna at sufficient power to enable reception by the external receiver device. In a third embodiment, the relay mechanism may be an external antenna so that the data transmissions may be passively re-radiated from the external antenna.

FIG. 1 illustrates a communication system including an embodiment transdermal antenna 110. The transdermal antenna 110 is partially inserted into a body cavity 108 to receive data transmissions from cameras 106 located inside of the body cavity 108 and relay the data transmissions to an outside receiving device 119. As illustrated in FIG. 1, a mammalian body 100 may include a skin layer 101, fat layers 104, muscle layers 102, and an inflated cavity 108 in the body which is created for the surgery by injecting air into the cavity via an inflation needle (not shown). During some surgical procedures, such as in laparoscopic surgeries, devices such as cameras 106 may be placed inside of the body cavity 108 to allow surgeons to view the organs on which they are operating without having to make large surgical incisions through the patient's skin. The cameras 106 may capture images from the inside of the body cavity 108. To transmit large amounts of data as required for high performance cameras 106, the cameras 106 may output a 1.5 Gbit per second data stream via a high frequency wireless communication link.

To receive high frequency signals that may be transmitted from equipments placed inside of a body cavity 108, the transdermal antenna 110 may be partially inserted inside of the body cavity 108 so that a portion 113 extends outside the body. The transdermal antenna 110 may receive the data transmissions 109 from the internal cameras 106 via an inner antenna 115 and conduct the radio frequency energy to an outer transceiver 112 or coupling circuit which relays the data transmissions to receiving devices 119 outside of the body 100. The data transmissions relayed by the transdermal antenna 110 may be received at an external transceiver 119 and provided to a display 122 which displays the camera images for the surgeon.

The transdermal antenna 110 may include a shaft 200 having a proximal end 111 which is inserted into a body cavity 108 and a distal end 113 which remains outside of the mammalian body 100. For ease of reference, the end of the transdermal antenna 110 inserted into the body 100 is referred to herein as the proximal end (proximal to the patient) and the other end is referred to as the distal end (distal from the patient). The data transmissions received by the inner antenna 115 may be conducted to the outer antenna 116 through a coaxial cable, a waveguide or a combination of coaxial cables and waveguides. The inner antenna 115 may be any form of antenna suitable for receiving radio frequency energy with frequencies in the range emitted by the internal cameras 106. For example, the figures illustrate the inner antenna 115 as a simple monopole antenna that may function as an omni-directional antenna. However, the antenna configurations shown are for illustration purposes only and any known antenna type or configuration may be used that is consistent with the frequencies emitted by the internal devices (e.g., internal cameras 106) and the dimensions and configuration of the transdermal antenna 110.

The received data transmissions may be relayed to the receiver device 119 wirelessly or via a wire connection. As shown in FIG. 1, the transdermal antenna 110 may conduct the received data transmissions using a cable 118 (e.g., a coaxial cable) or waveguide that may directly connect the distal end 113 of the transdermal antenna 100 to an external receiver device 119. In some embodiments a transceiver 112 may be coupled to the transdermal antenna including circuitry for receiving, amplifying and conducting the received radio frequency energy onto the cable 118 for conduction to the receiver device 119. In other embodiments, a simple conductor connection may be provided so that received radio frequency energy are efficiently coupled to a cable 118 for conduction to the external receiver 119.

The transdermal antenna 110 with an inner antenna 115 and an external transceiver 112 may also be used to transmit control signal from an external camera control panel to the wireless cameras within the body cavity 108. Such control signals may control camera parameters such as zoom, focus and lighting, and may also control camera viewing angle and position (e.g., in case of a magnetically floating camera). The data rate of the data going into the body cavity will typically be much lower than the data rate of the video coming out.

In an alternative embodiment, the transdermal antenna 110 may re-transmit received data wirelessly using a transceiver 112 coupled to an outer antenna 116. In this embodiment, the transceiver 112 receives radio frequency energy from the transdermal antenna and rebroadcasts the signal at sufficient power for reception by the external receiver 119.

The use of an outer antenna 116 attached to the distal end of the shaft 200 is discussed in more detail below with reference to FIGS. 9-11.

The transdermal antenna 110 may include a stopper 114 to prevent the entire transdermal antenna 114 from inadvertently falling into the body cavity 108. The stopper 114 may also provide a handle for use by the surgeon.

Figure 2:
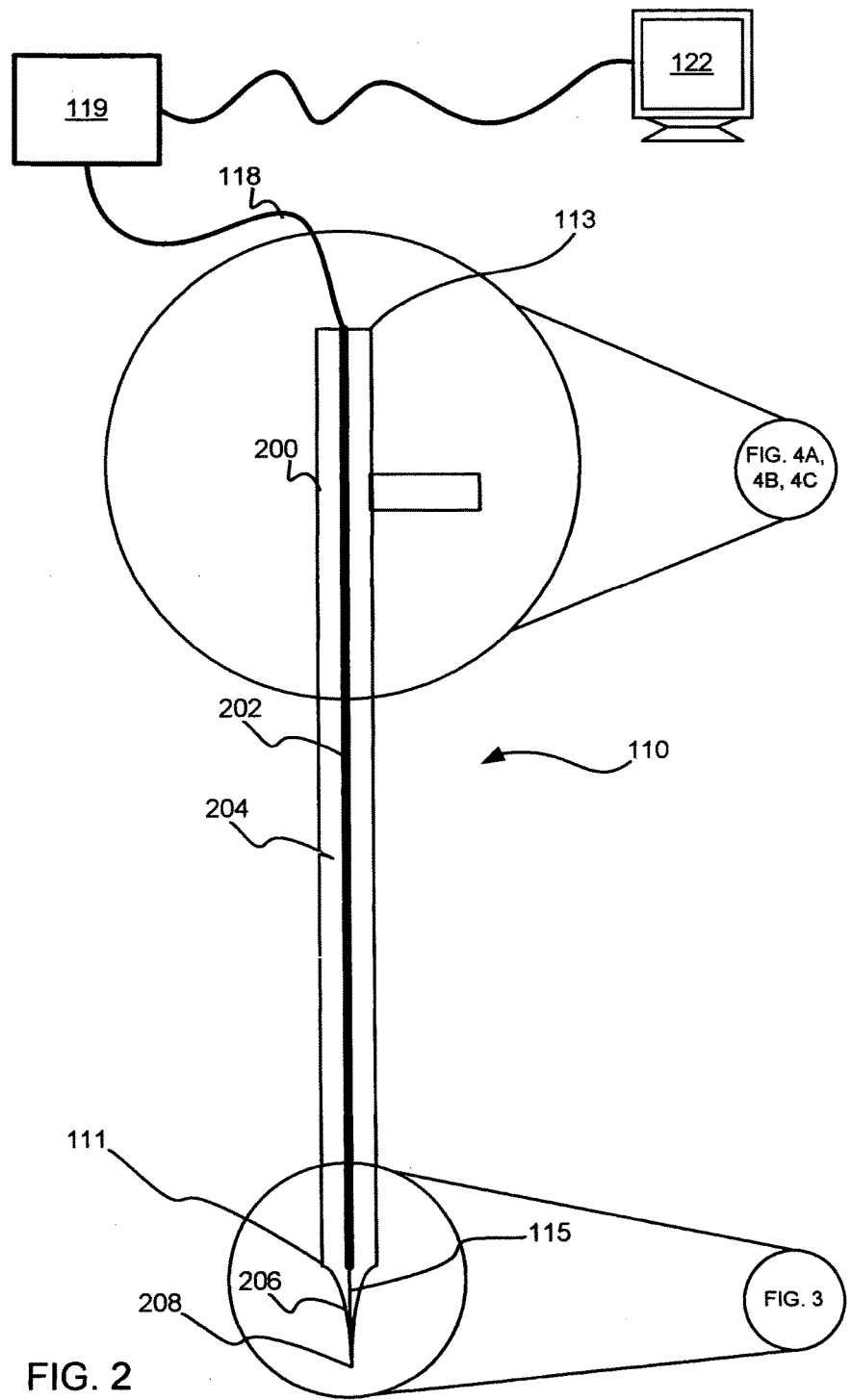
FIG. 2 is a cross sectional view of a transdermal antenna connected to an external receiver device via wire connection according to an embodiment.

The transdermal antenna 110 may be designed in different ways. FIG. 2 illustrates a first embodiment, showing a cross sectional view of a transdermal antenna 110 that relays data signals to an external receiver device 119 by conducting them via an external cable 118. As illustrated in FIG. 2, a transdermal antenna 110 may include a shaft 200 having a lumen 204, a proximal end 111, and a distal end 113. As discussed above, the transdermal antenna 100 may be connected to an external receiver device 119 via a wire connection 118 at the distal end 113 of the shaft 200. The transdermal antenna 110 may further include a tip portion 206 at the proximal end 111 of the shaft 200. The distal end of the tip portion 206 may be fixedly attached to the proximal end 111 of the shaft 200. The proximal end of the tip portion 206 may be tapered to a point 208 to facilitate pushing of the transdermal antenna 110 into the body 100. The tip portion 206 may be formed by tapering the shaft 200 at the proximal end 111.

The transdermal antenna 110 may further include a coaxial cable 202 placed inside the lumen 204 of the shaft 200. The coaxial cable 202 may extend from the proximal portion to the distal portion of the transdermal antenna 110. At the proximal end, the coaxial cable 202 may form the inner antenna 115 that may extend beyond the proximal end 111 of the shaft 200 and into the tip portion 206. The inner antenna 115 may be configured to receive data transmissions from devices located within the body cavity 108 and conduct the data transmissions to the external cable 118 via the internal coaxial cable 202. At the distal end 113 of the shaft 200, the coaxial cable 202 may connect with an external cable 118 (e.g., a coaxial cable) which conducts the data signals to a receiver device 119 located outside of the body 100. In the embodiment illustrated in FIG. 2, the external cable 118 may connect to the distal end 113 of the transdermal antenna 110 via a connector (as shown in more detail in FIG. 4B) or the external cable 118 and the transdermal antenna 110 may be configured as a unit with the internal coaxial cable 202 continuing into the external cable 118. The external receiver device 119 may process the received data and provide image data to a display 122 which displays images for the surgeon.

Figure 3:
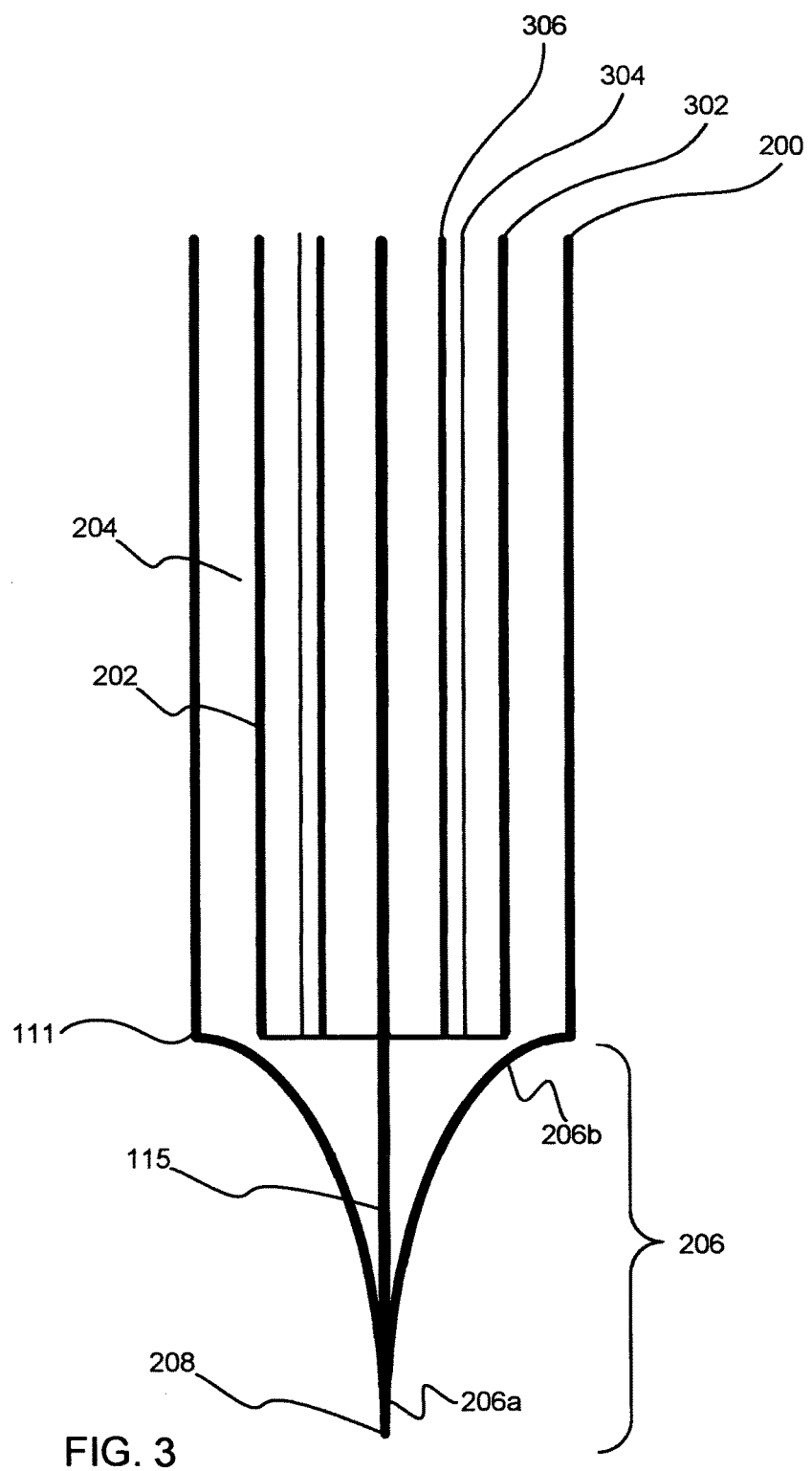
FIG. 3 is a detailed cross sectional view of the proximal portion of a transdermal antenna according to an embodiment.

FIG. 3 shows a detailed cross sectional view of the proximal portion of an embodiment of the transdermal antenna 110. A coaxial cable 202 located within the lumen 204 of the shaft 200 may comprise several layers including a conductor core 308, an inner insulator 306 covering the conductor core 308, a conductive screen 304 covering the inner insulator 306 and an outer plastic sheath 302 covering the entire contents of the coaxial cable 202. As the coaxial cable 202 approaches the tip portion 206, the outer plastic sheath 302, the inner insulator 304 and the conductive screen 306 may end before the conductor core 308, so the conductor core 308 continues into the tip 206. Such an extension of the conductor core 308 of a coaxial cable 202 may be used to form the inner antenna 115 in the tip 206. As mentioned above, the illustration of the inner antenna 115 as a monopole antenna formed by extending the conductor core 308 is only one example of a suitable antenna configuration that may be use, and the inner antenna 115 may be any known form or configuration of antenna. In another embodiment, the coaxial cable 202 may comprise an outer conductive tube, an inner conductive core and a dielectric material filling the space there between.

The tip 206 may have different designs. For example, the tip 206 may be tapered at its proximal end 206a. Such a configuration allows the tip 206 to form a sharp needle point 208 at the proximal end 206a. A sharp point 208 may enable a surgeon to easily pierce the skin, fat and muscles of the body 100 to insert the transdermal antenna 110 into a body cavity 108. Alternatively, the tip may be blunt (not shown), in which case an incision may be required to insert the transdermal antenna 110 into the body 100.

The tip 206 region may or may not be a part of the shaft 200. If the tip 206 is part of the shaft 200, it may be constructed of the same material as used in the shaft 200 provided the shaft 200 is made of a dielectric material such as plastic. If the tip 206 is an attachment to the shaft 200, it may be fixedly or removably attached to the proximal end 111 and be constructed of a material different from that of the shaft 200. For example, the tip 206 may be constructed of a dielectric material, such as resin or plastic.

To facilitate piercing of the body 100, the tip 206 and the proximal portion of the shaft 200 may be covered by a lubricating substance such as silicone. A lubricate coating may allow the transdermal antenna 110 with a needle point 208 to pierce through the body 100 easier and thus render the procedure more efficient and safe.

Figure 4A:
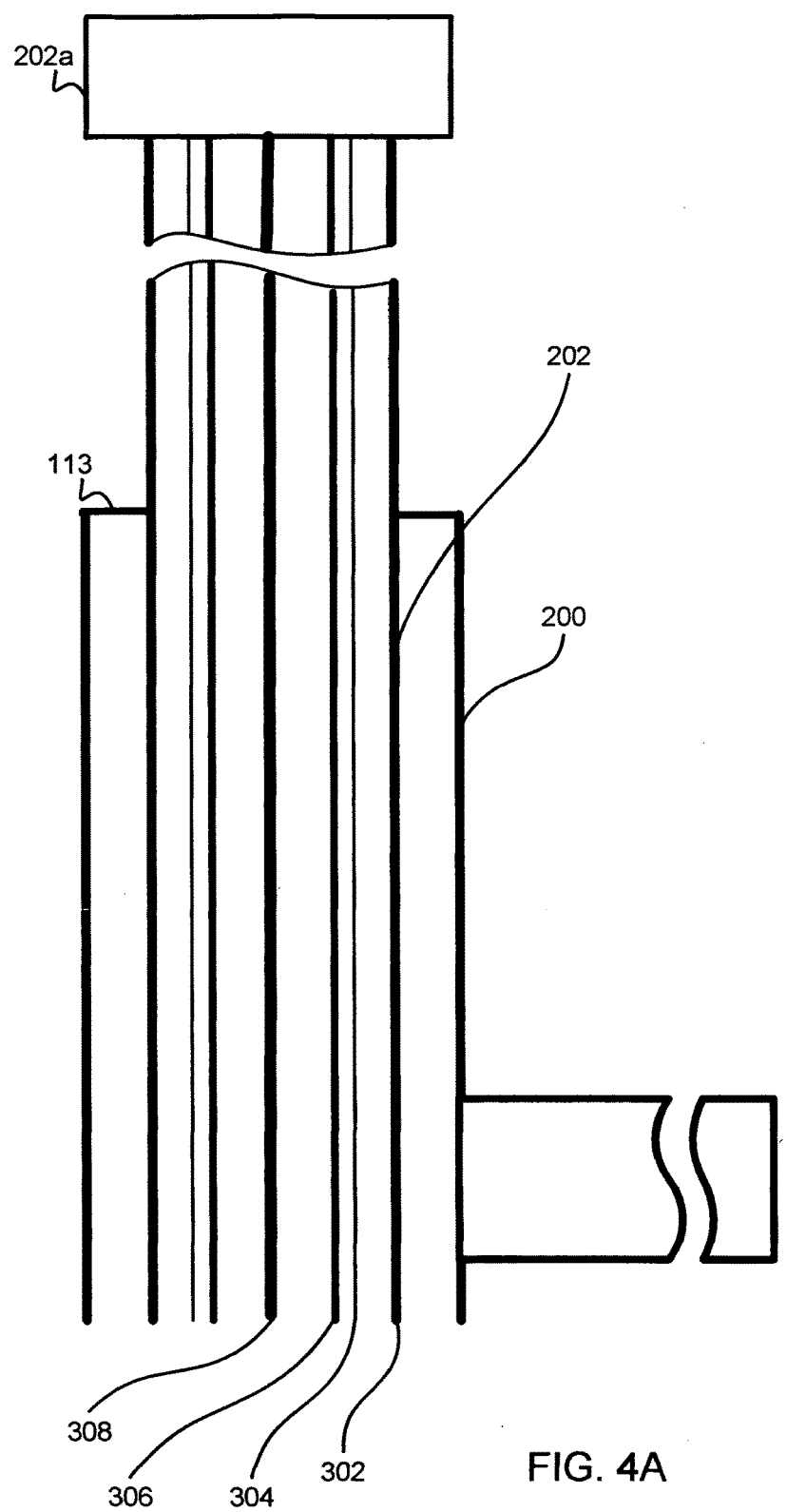
FIG. 4A-4C are detailed cross sectional views of the distal portions of a transdermal antenna according to an embodiment.
Figure 4B:
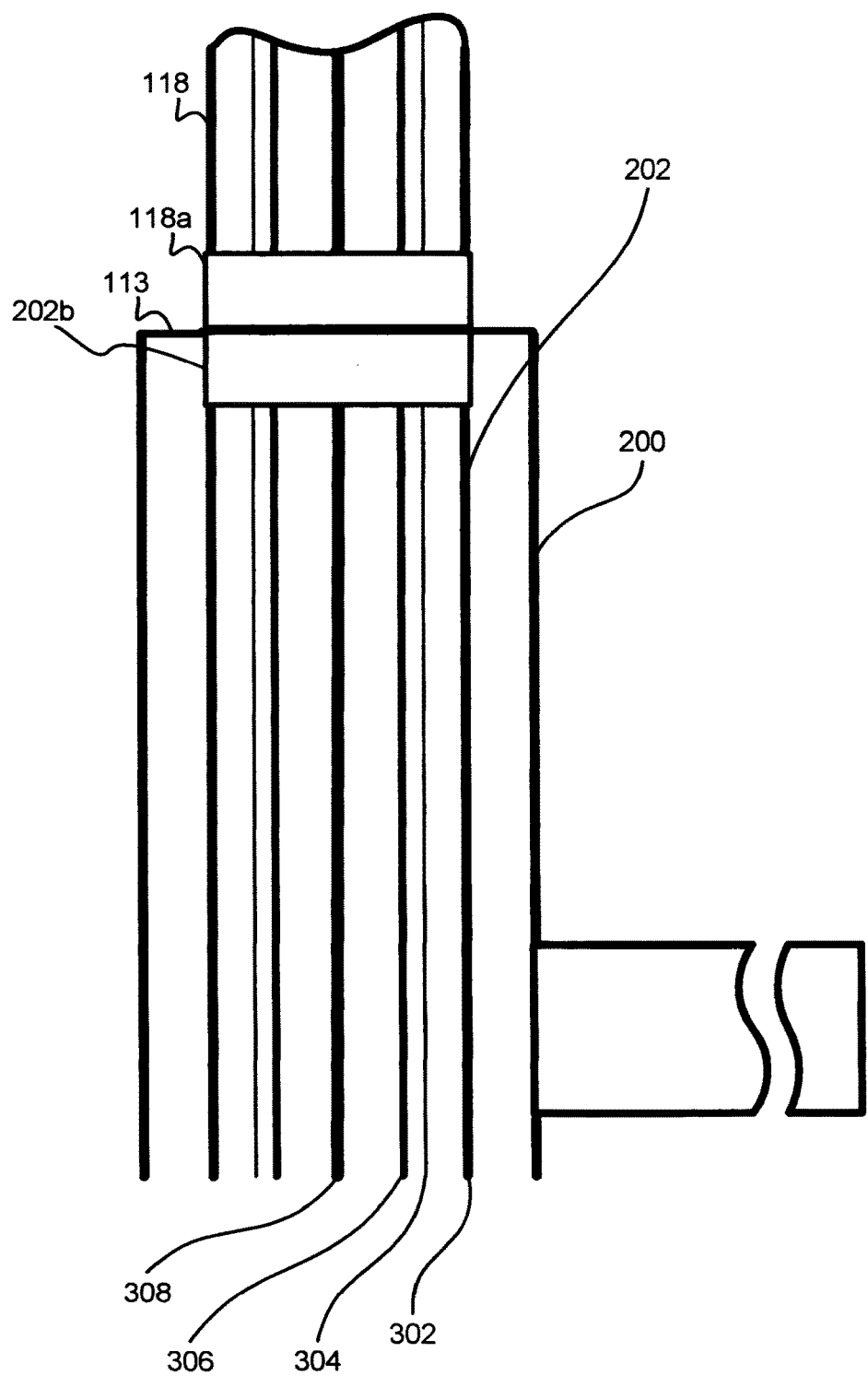
Figure 4C:
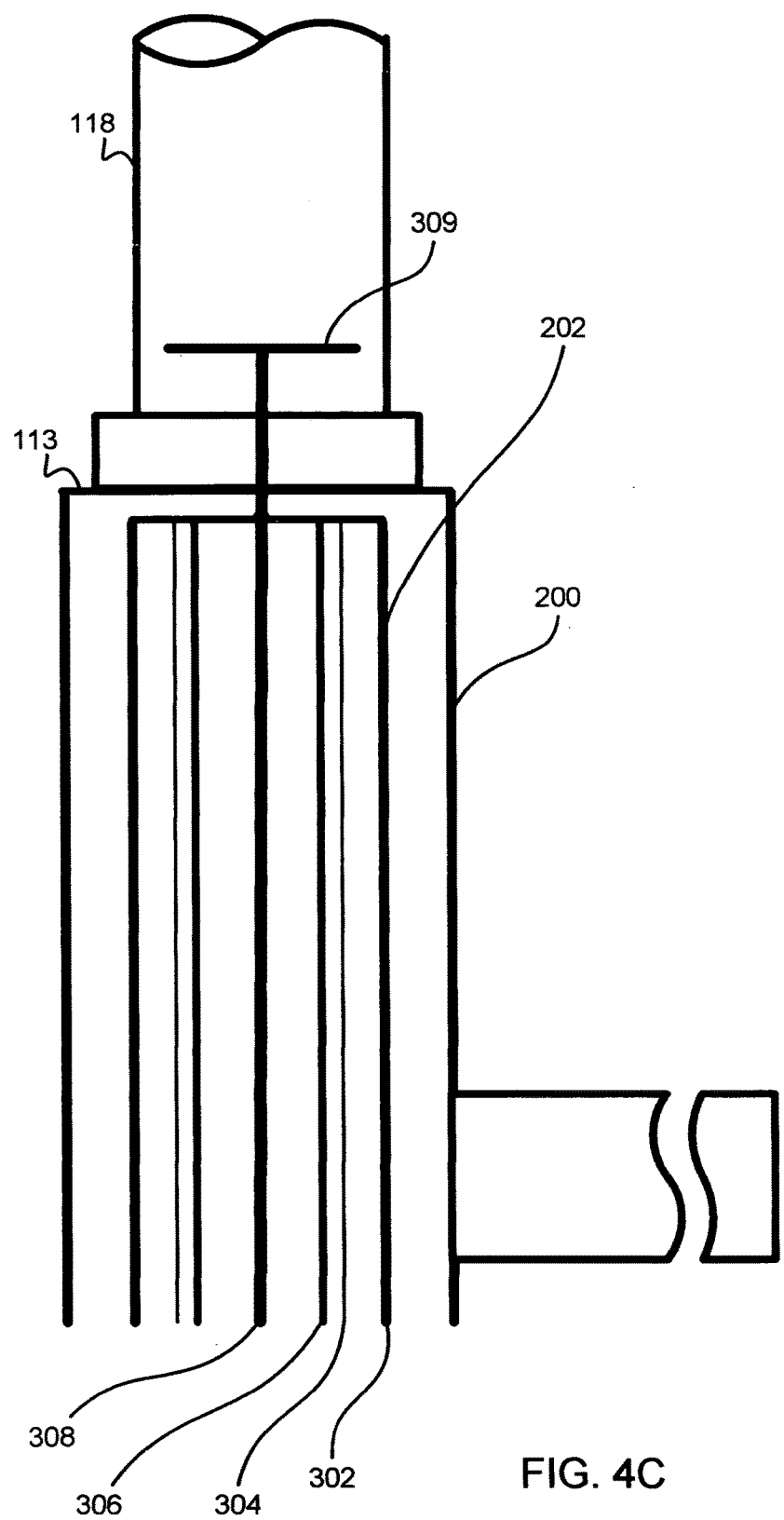

FIGS. 4A-4C illustrate details of the distal (i.e., external) portion of two embodiments of the transdermal antenna 110 which connect to a receiver device 119 via a wired connection 118 that may be any known physical connection that will enable conduction of data from the transdermal antenna 110 to a receiver device 119, such as a coaxial cable or a waveguide.

To enable the transdermal antenna 110 to be coupled to an external cable 118, the internal coaxial cable 202 may be extended beyond the transdermal antenna 110 to form the external cable 118, as illustrated in FIG. 4A. In such a configuration, the external cable 118 may terminate in an electrical connector 202a for connecting to the external receiver device 116. The electrical connector 202a may be any known electrical connector including a conventional coaxial cable connector.

In a further embodiment illustrated in FIG. 4B, an external coaxial cable 118 may be connected to the transdermal antenna 110 via a cable connector 202b on the internal coaxial cable that couples to a cable connector 118a on the external cable 118. In this embodiment, the internal coaxial cable 202 may end at the distal end 113 of the shaft 200 by forming an electrical conduction connection to the distal end cable connector 202b. Likewise the proximal end of the coaxial cable 118 terminates in a cable connector 118a configured to connect to the transdermal antenna 110 cable connector 202b. Once a connection is established between the two cable connectors 202b, 118a, data transmissions received by the inner antenna 115 and conducted through the coaxial cable 202 of the transdermal antenna 110 can be conducted to the external receiver device 119.

In a further embodiment illustrated in FIG. 4C, a waveguide may be used as the external cable 118. In such an embodiment, the conductor core 308 may extent beyond the terminus of the coaxial cable 202. The conductor core 308 of the transdermal antenna 110 may extend into the external waveguide cable 118. Data transmissions received by the inner antenna 115 and conducted along the length of the coaxial cable 202 will be conducted into the waveguide 118 by a cable-to-waveguide transition antenna 309 coupled to the extended conductor core 308. Another embodiment design uses the entire transdermal shaft as a round waveguide. In this embodiment the shaft may be filled with air or with a dielectric material. At both ends of the shaft an adaptor may be included to couple the signal from the waveguide to the antenna at the proximal end and from the waveguide to a coaxial cable at the distal end.

Figure 5:
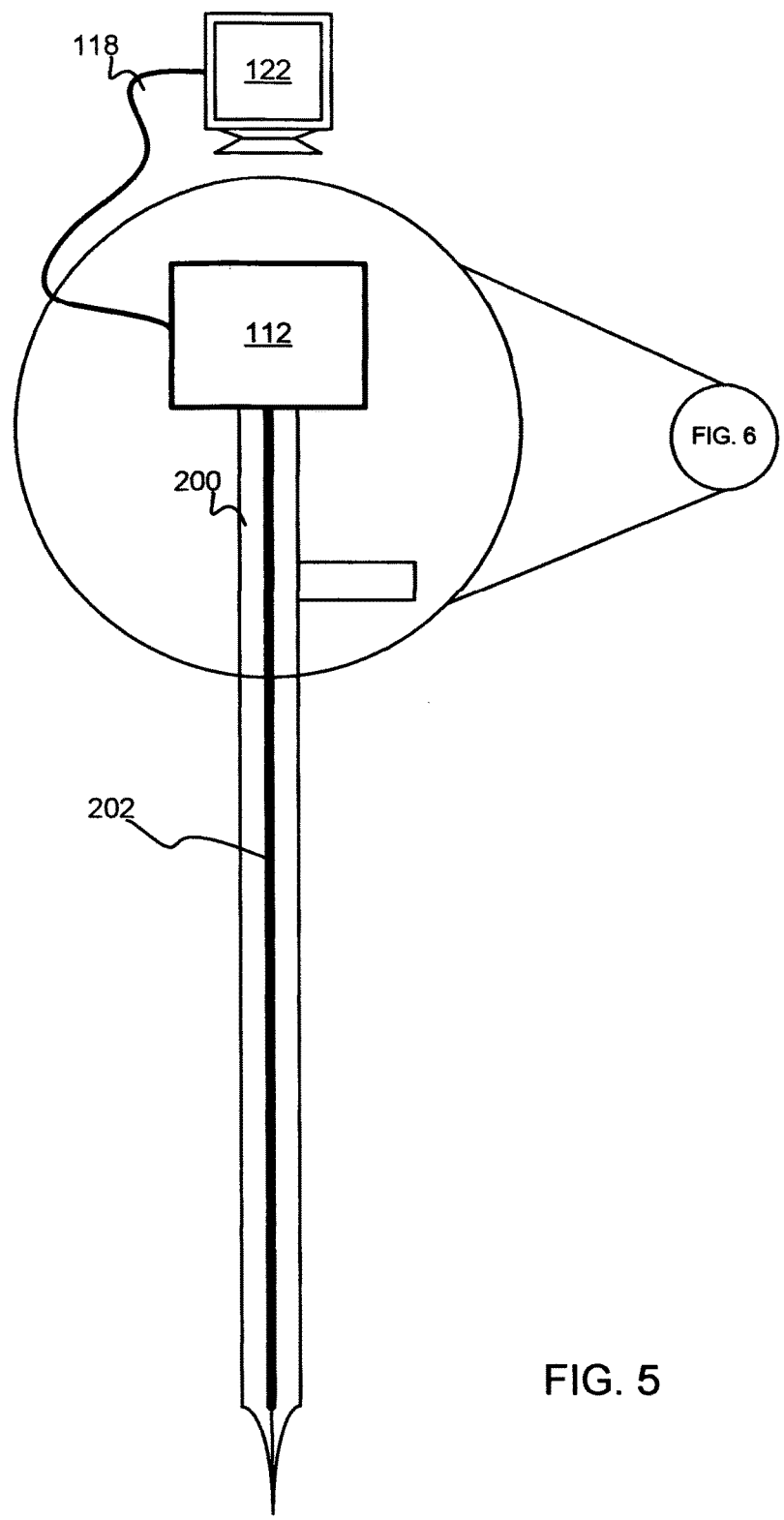
FIG. 5 is a cross sectional view of a transdermal antenna with a transceiver coupled to an external receiver device according to an embodiment.
Figure 6:
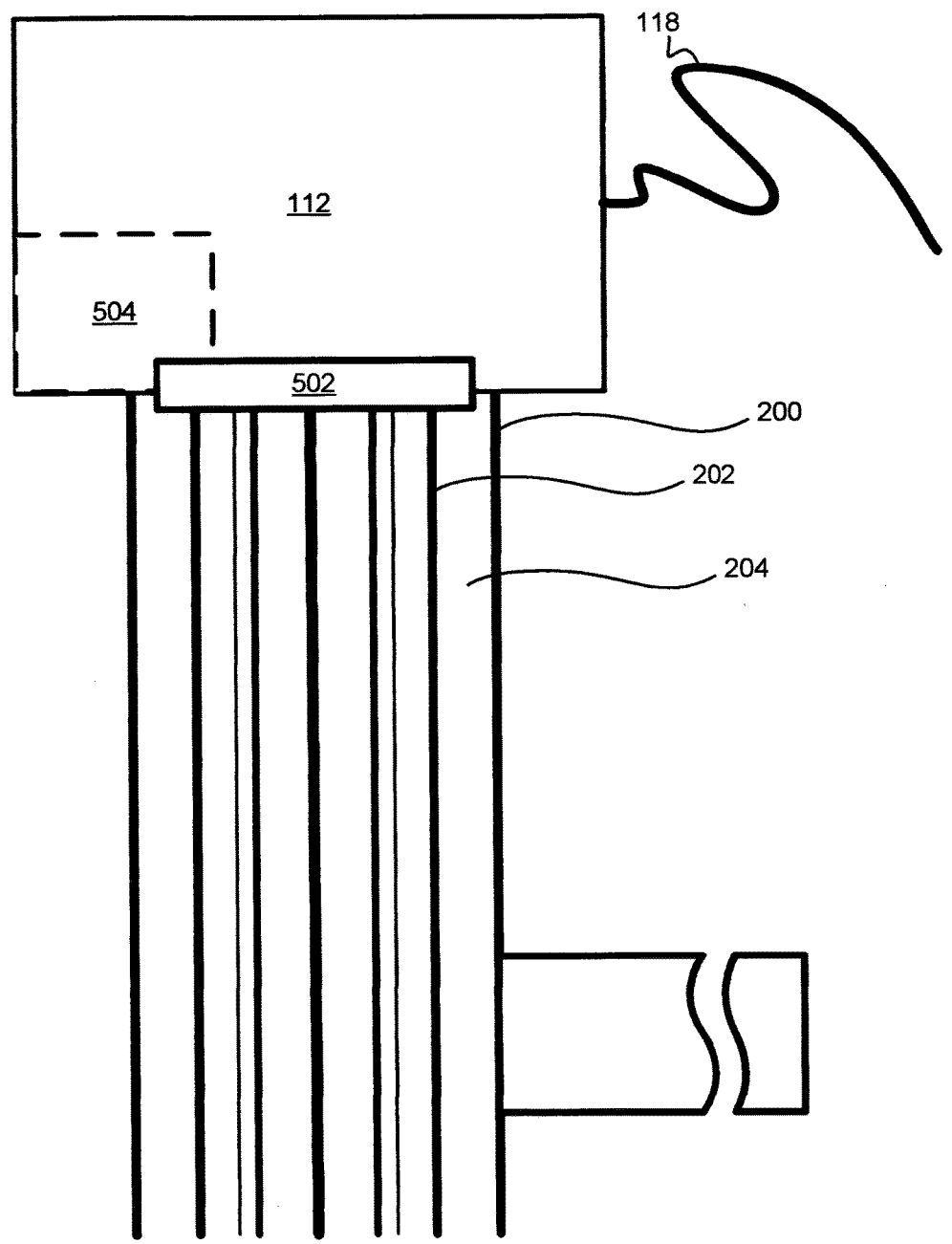
FIG. 6 is a detailed cross sectional view of the distal portion of a transdermal antenna including a transceiver according to an embodiment.

FIGS. 5 and 6 illustrate cross sectional views of an alternative embodiment transdermal antenna 110 in which a transceiver 112 on the exterior end of the antenna couples received transmission signals and relays the signals to the external cable 118.

FIG. 5 illustrates an embodiment transdermal antenna 110 in which the transdermal antenna 110 includes a transceiver 112 connected at the distal portion. The transceiver 112 is configured to receive high data rate video data transmissions from the coaxial cable 202 and relay those signals to the wire connection 118 which conducts the signals to the receiver device 122 and to transmit lower data rate control signals from a control panel into the coaxial cable 202. In this embodiment, the transceiver 112 may include circuitry to receive and enhance the transmission signals (e.g., by amplifying the signals) and efficiently applying them to the external cable 118 for conduction with low loss.

FIG. 6 illustrates details of the distal portion of the transdermal antenna 110 embodiment described above with reference to FIG. 5. The transceiver 112 may be attached to the distal end 113 of the shaft 200 and connected to the coaxial cable 202 via a connection device 502. Data transmissions received from devices within the patient's body 100 may be conducted through the internal coaxial cable 202 and received by the transceiver 112. The transceiver 112 may relay the data transmissions to an outside receiver device 119 by conducting them onto the external cable 118. The transceiver 112 may also receive power from an external power supply through the cable 118, such as to power an amplifier circuit. Optionally, the transceiver may receive power from an internal power source 504, such as a battery, housed within the transceiver 112.

Figure 7:
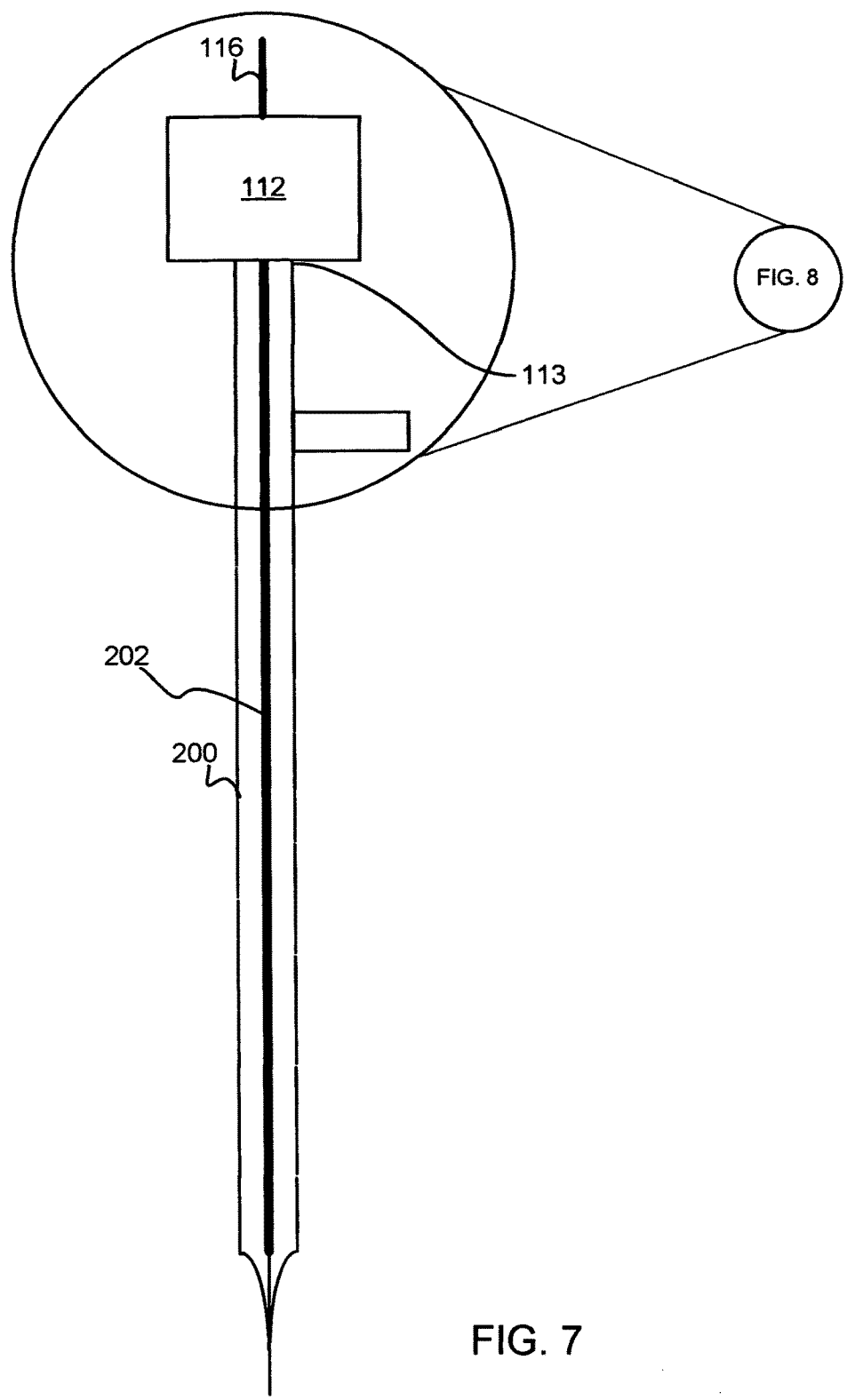
FIG. 7 is a cross sectional view of a transdermal antenna including a wireless transceiver according to an embodiment.
Figure 8:
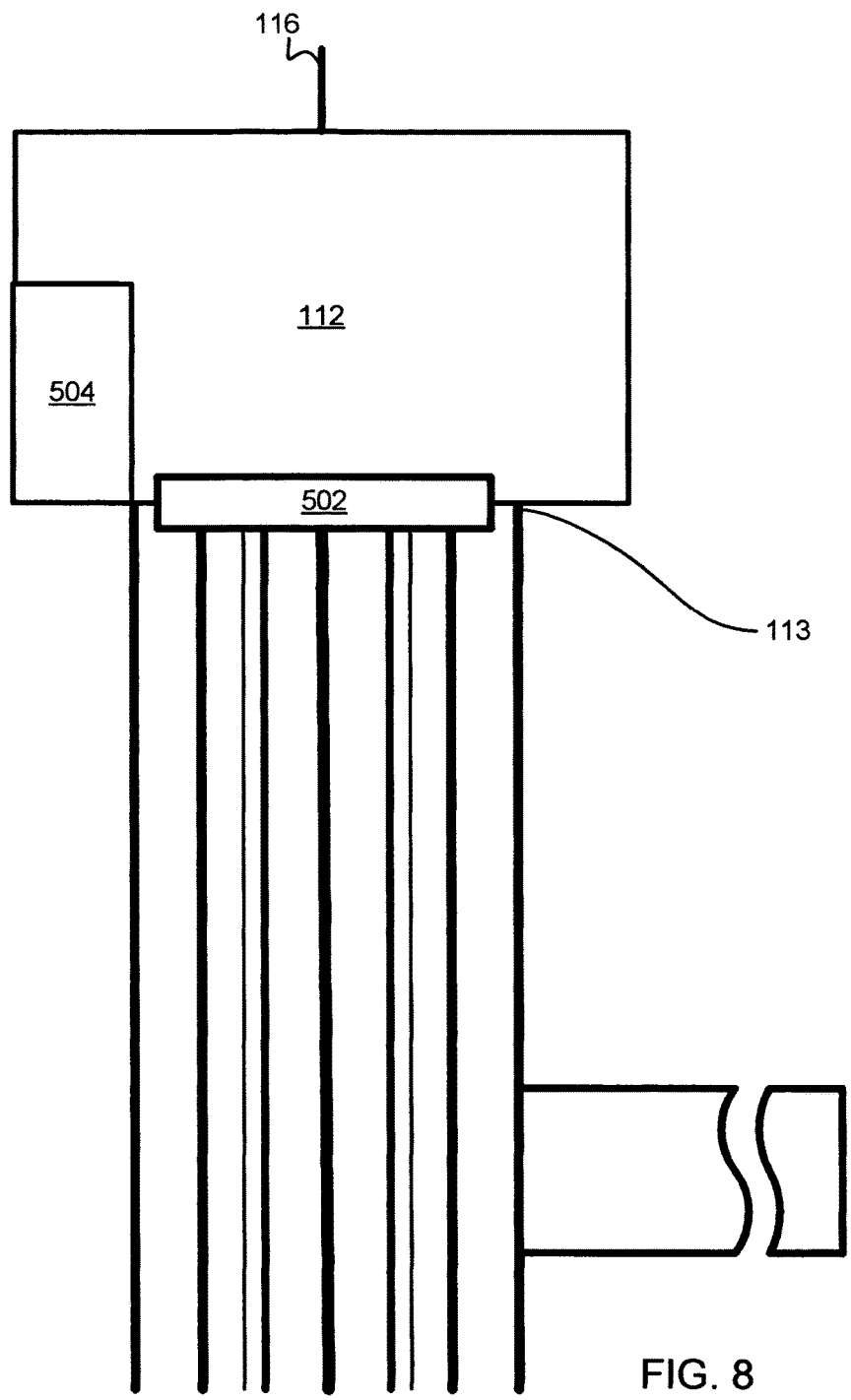
FIG. 8 is a detailed cross sectional view of the distal portion of a transdermal antenna including a wireless transceiver according to an embodiment.

FIGS. 7 and 8 illustrate cross sectional views of an alternative embodiment transdermal antenna 110 in which a transceiver 112 on the exterior end re-transmits received transmission signals as wireless signals emitted from an external antenna 116. Referring to FIG. 7, the transceiver 112 may be connected to the distal portion of the transdermal antenna 110 to receive data transmissions from the internal coaxial cable 202. The transceiver 112 may amplify and re-transmit the date transmissions wirelessly via the external antenna 116. The transceiver 112 may be configured to establish a wireless data link connection with an external receiver device 119 using a known high data rate wireless communication protocol. Further, the transceiver 112 may be configured to reformat or tunnel the received data transmissions to facilitate re-transmission via an external wireless data link connection.

FIG. 8 illustrates details of the distal portion of the transdermal antenna 110 described above with reference to FIG. 7. The transceiver 112 positioned at the distal end 113 of the shaft 200 is connected to the coaxial cable 202 via a connection device 502. The transceiver 112 may be any known electronic receiver and transmitter circuit capable of supporting a high upstream data rate and a lower downstream rate. Further, the transceiver 112 may receive power from an internal power source 504, such as a battery, housed within the transceiver 112.

Figure 9:
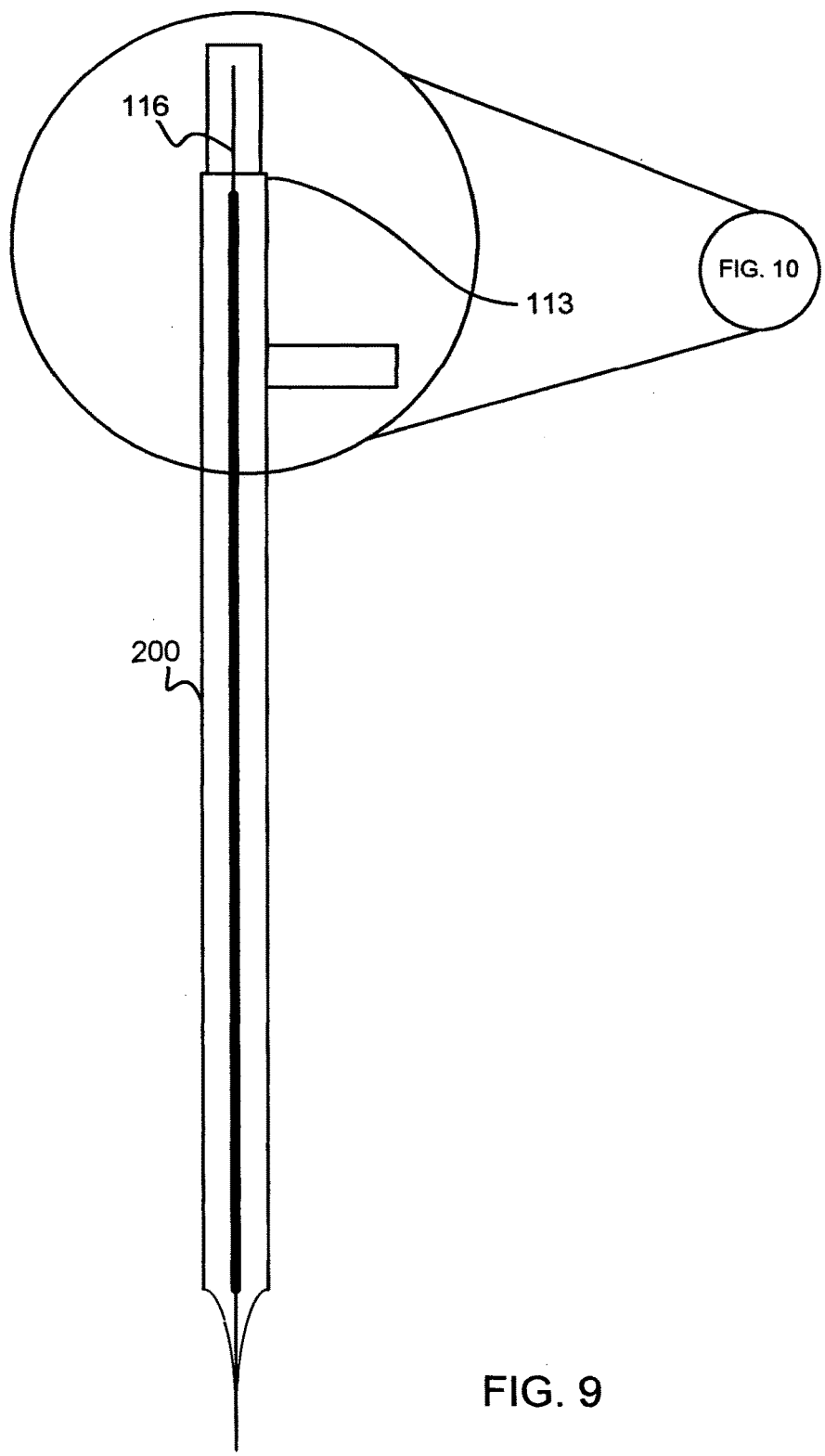
FIG. 9 is a cross sectional view of a transdermal antenna including an external antenna according to an embodiment.
Figure 10:
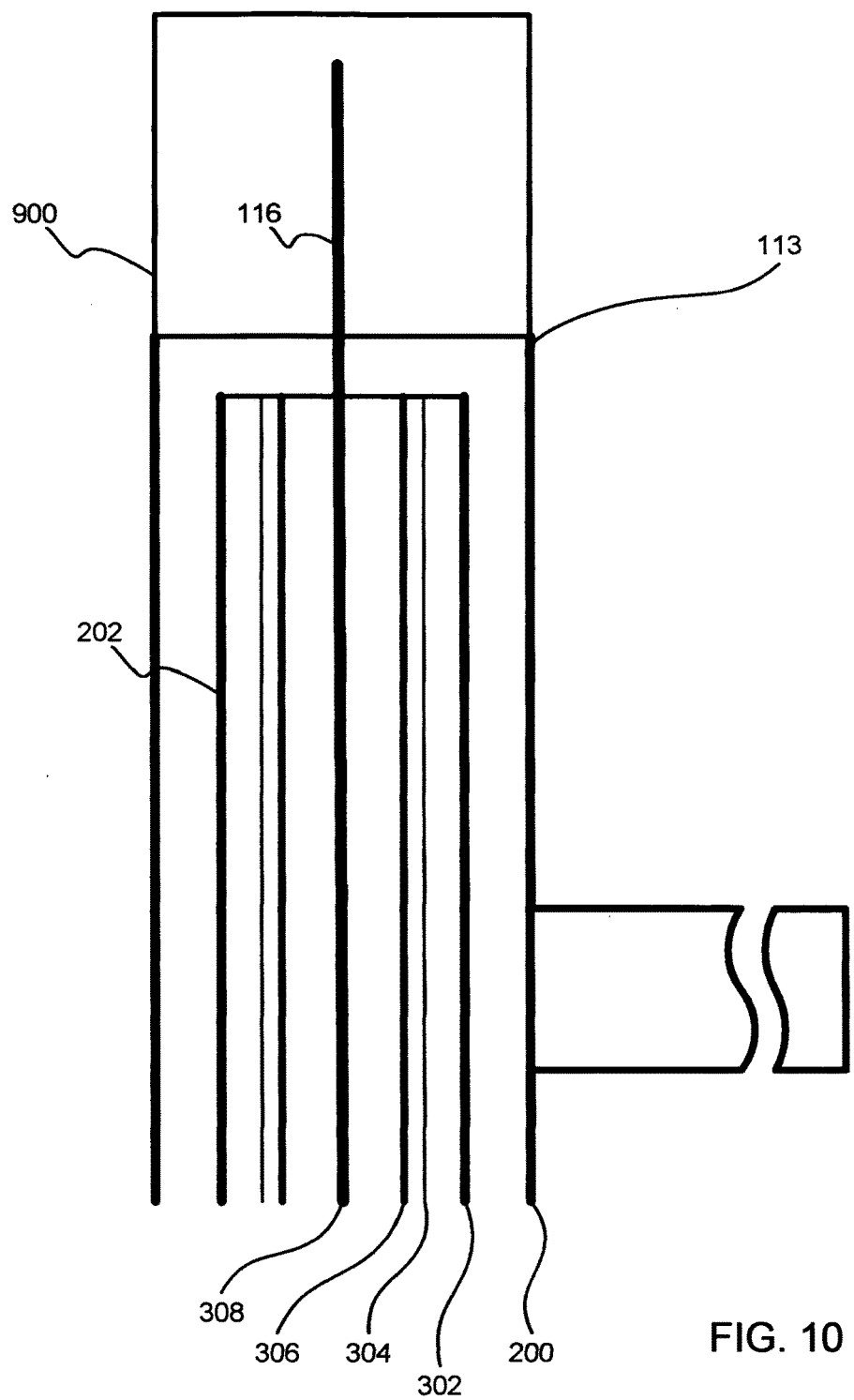
FIG. 10 is a detailed cross sectional view of the distal portion of a transdermal antenna including an external antenna according an embodiment.
Figure 11:
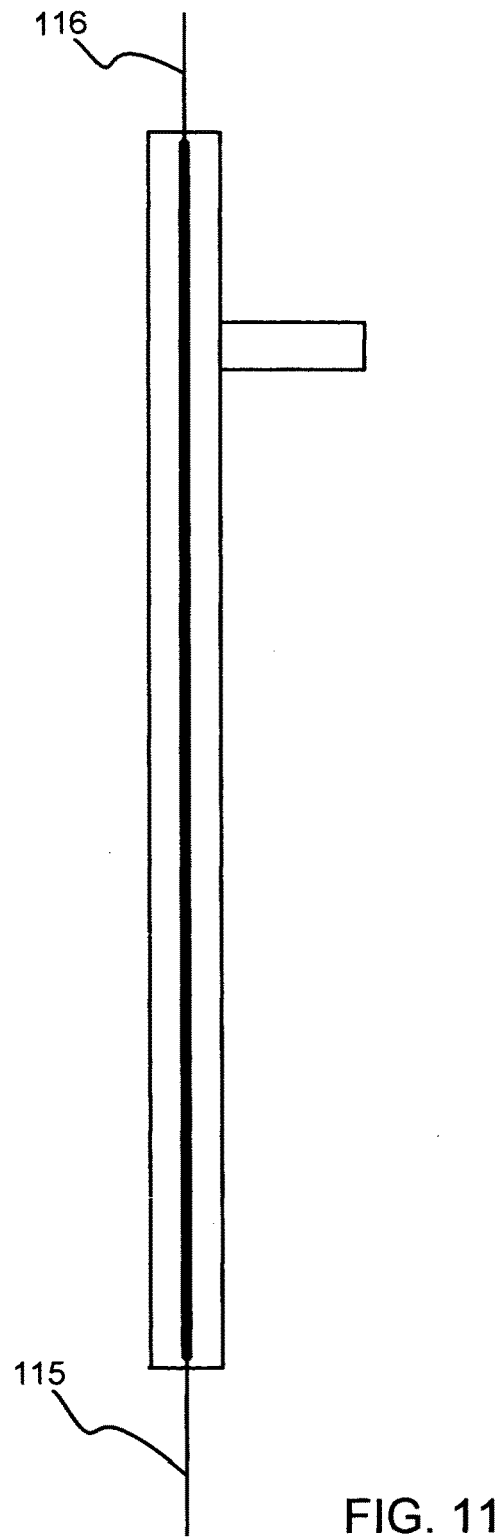
FIG. 11 is a cross sectional view of a transdermal antenna according to another embodiment.

FIGS. 9-11 illustrates an alternative embodiment transdermal antenna 110 that includes an outer antenna 116 coupled to the coaxial cable 202 at the distal end of the shaft 200 configured to re-radiate transmission signals received via the internal antenna 115. This embodiment provides a simple (and thus potentially less expensive) transdermal antenna configuration since relaying of transmission signals is accomplished passively by re-radiation from the external antenna 116. This embodiment will yield a lower strength wireless signal outside the body compared to embodiments including a transceiver 112. Therefore this embodiment may require the external receiver device 119 to be positioned closed to the transdermal antenna, such as resting on the skin of the patient immediately adjacent to or covering the transdermal antenna 110. Further, in order to provide sufficient re-radiated signal strength, the internal antenna 115 may need to have a high gain configuration and/or the wireless devices positioned within the patient's body may need to transmit data with a higher signal strength.

FIG. 10 illustrates details of the distal portion of the transdermal antenna 110 shown in FIG. 9. This embodiment transdermal antenna 110 includes an outer antenna 116 fixedly attached to the distal end of the shaft 200. To form the outer antenna 116, the conductor core 308 may extend beyond the terminus of the rest of the coaxial cable 202 into the tail portion 900. Data transmissions received from devices inside of the body 100 and conducted through the coaxial cable 202 will be re-radiated from the outer antenna 116. A receiver device antenna (not shown) may be positioned close to the outer antenna 116 to receive the re-radiated signals and convey them to an external receiver device 119. To provide sufficient link budget for reliably re-radiating data transmissions to a receiver device 119, a device located inside of the body, such as a camera 106, may need to emit higher power signals than is the case for the embodiments described above with reference to FIGS. 2-8. Also, the transdermal antenna 110 may include a high gain interior antenna 115. Further, the external receiver device antenna may be configured to fit over the top of the transdermal antenna, such as a cap (not shown) including an antenna so that all emitted radiation is received by the receiver antenna. Such a cap may also serve hygienic purposes by covering the puncture formed by the transdermal antenna.

The top portion of a re-radiation transdermal antenna may include a cover 900 to protect the outer antenna 116 from damage. The cover 900 may be constructed from a dielectric material, such as resin or plastic.

FIG. 11 illustrates an embodiment transdermal antenna 110 in which the inner antenna 115 and the outer antenna 116 are not covered by protective coverings. To protect the inner antenna 115 from being damaged during insertion into the body in such an embodiment, an incision may be made using a scalpel prior to inserting the proximal portion of the transdermal antenna 110 into the body 100.

Figure 12:
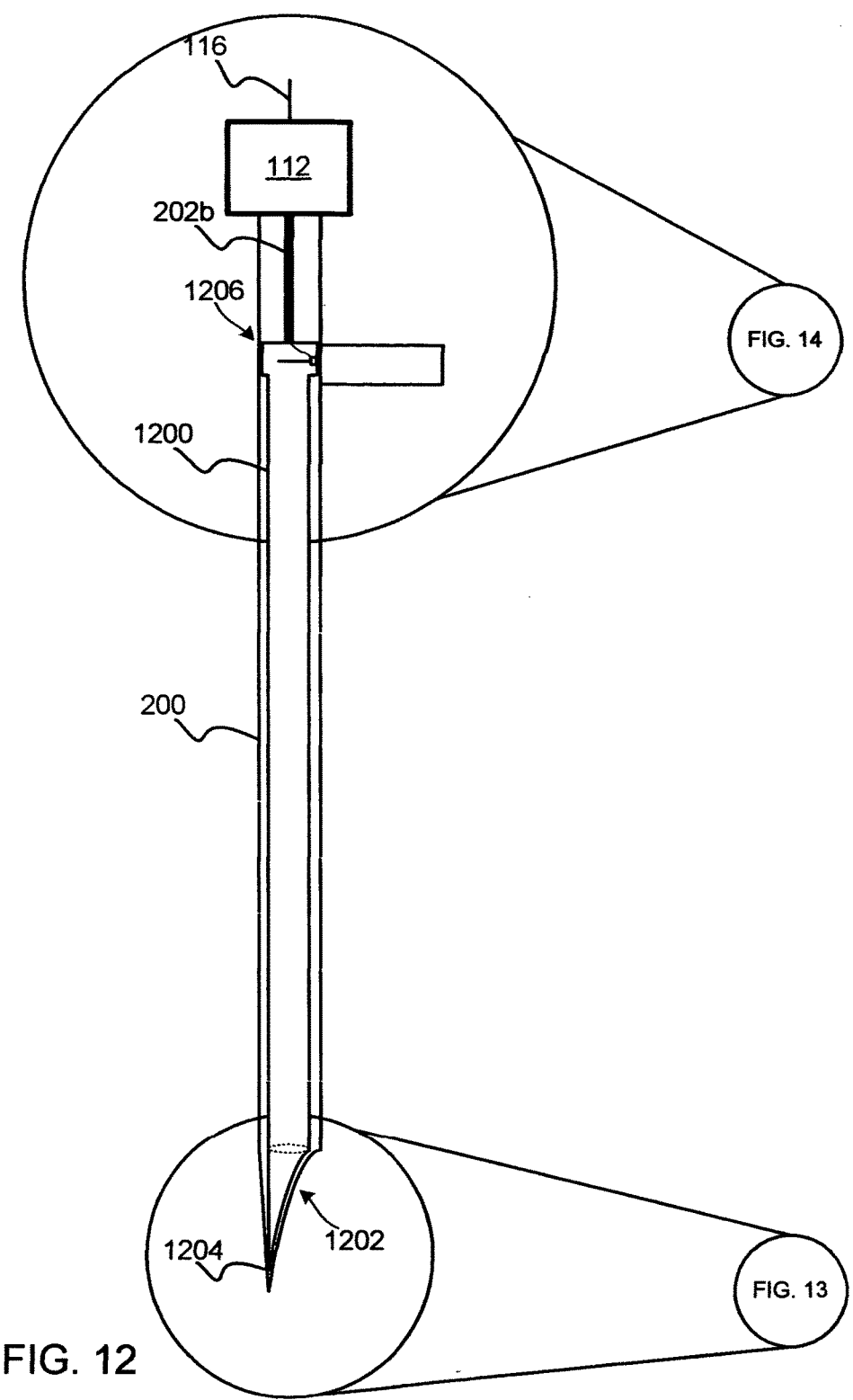
FIG. 12 is a cross sectional view of a transdermal antenna including a combination of a coaxial cable and a waveguide for conducting radio frequency signals according to an embodiment.

FIG. 12 illustrates an embodiment transdermal antenna 110 including a combination of a coaxial cable 202 and a waveguide 1200 to conduct data transmissions received via an opening 1202 at the proximal end to the transceiver 112 on the distal end. Data transmissions from devices inside of a body cavity 108 may be received by the opening 1202 which is configured to enable radio frequency radiation to enter into the waveguide 1200. The proximal end of the transdermal antenna 110 may be configured to form a sharp point 1204 to facilitate insertion into a body. The waveguide 1200 may conduct received data transmissions to a waveguide-to-coax transition 1206 which conducts received signals to an internal coaxial cable 202. The coaxial cable 202 conducts the data transmissions to a transceiver 112 where they may be received and retransmitted via an external antenna 116 or conducted via a cable 118 (not shown in FIG. 12) to an external receiver device 116.

Figure 13:
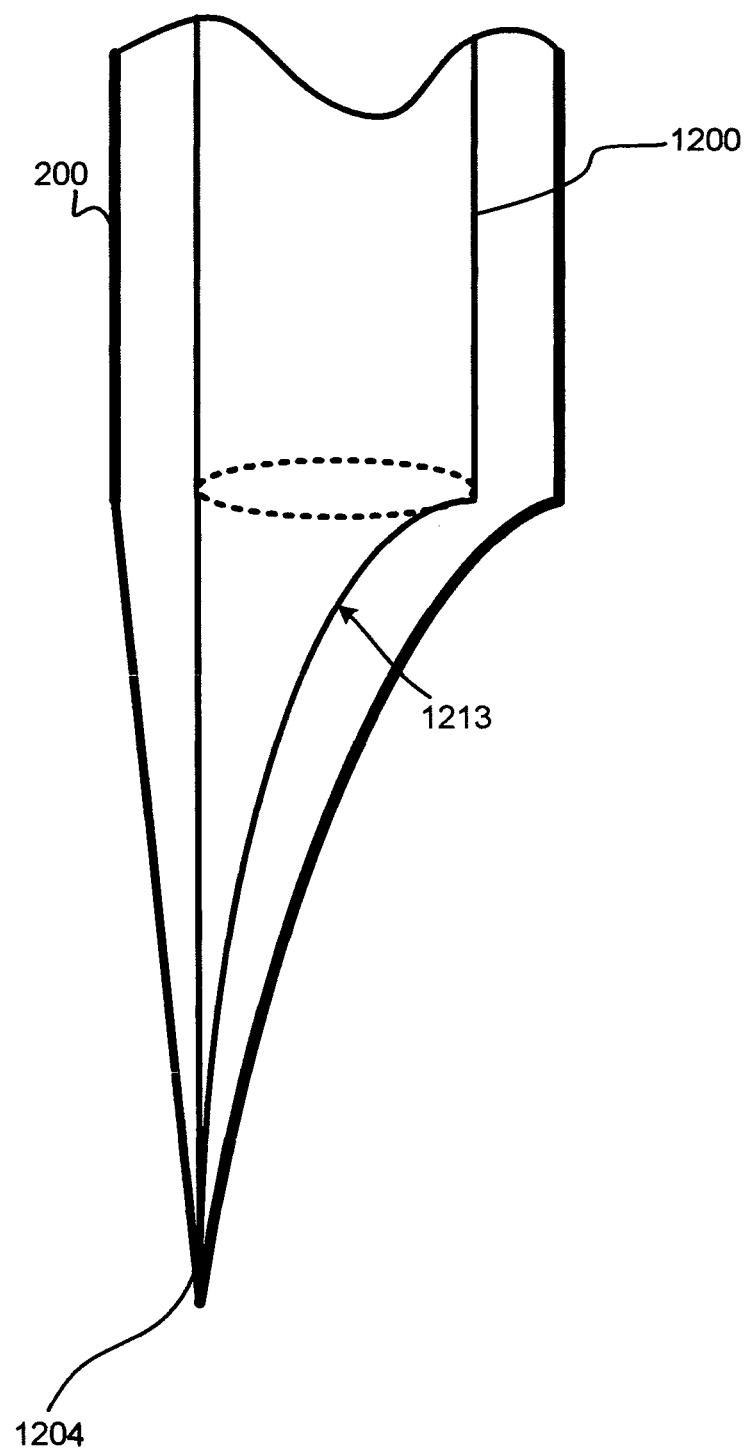
FIG. 13 is a detailed cross sectional view of the proximal portion of the transdermal antenna shown in FIG. 12.

FIG. 13 illustrates details of the proximal portion of the transdermal antenna 110 described above with reference to FIG. 12. The waveguide 1200 may terminate in an opening 1213 that is configured to radio frequency radiation to enter into the waveguide 1200. Data transmissions from devices inside of a body cavity 108 may be received via the waveguide opening 1213 so that the radio frequency energy is transmitted to the distal end of the waveguide 1200. As mentioned above, the exterior portion of the transdermal antenna 110 may be fashioned into a sharp point 1204 which also protects the end of the waveguide opening 1213 from damage during insertion into a patient's body.

Figure 14:
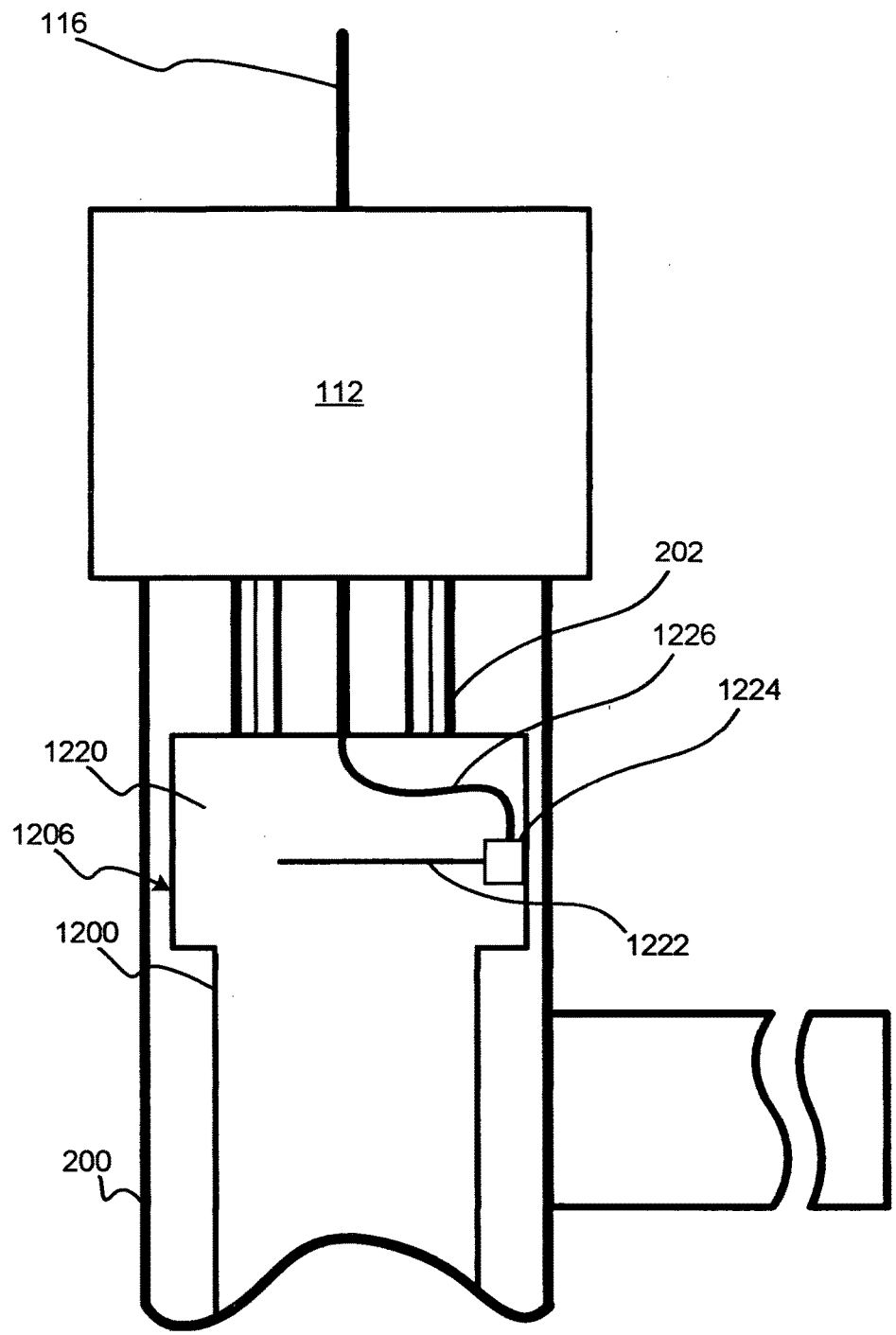
FIG. 14 is a detailed cross sectional view of the distal portion of a transdermal antenna shown in FIG. 12.

FIG. 14 illustrates details of the distal portion of the transdermal antenna 110 described above with reference to FIG. 12. At the distal portion the waveguide 1200 is coupled to a waveguide-to-coaxial-cable transition 1206 which receives RF energy from the waveguide and conducts the signal to a distal internal coaxial cable 202 for conduction to a transceiver 112 (or external coaxial cable 118). Designs for waveguide-to-coaxial-cable transitions 1206 are well known in the communication technology arts, and any of a number of suitable known transitions may be used in the various embodiments. Typically, a waveguide-to-coaxial-cable transition 1206 will include a chamber 1220 at the end of the waveguide 1200 which includes a probe 1222 that extends into the waveguide path to receive RF energy. The probe 1222 is connected to a center conductor 1226 of a connected coaxial cable 202. The waveguide-to-coaxial-cable transition 1206 may further include support structure 1224 to hold the probe 1222 in the proper position with the proper exposed length to achieve high-gain reception of RF energy from the waveguide 1200.

Figure 15A:
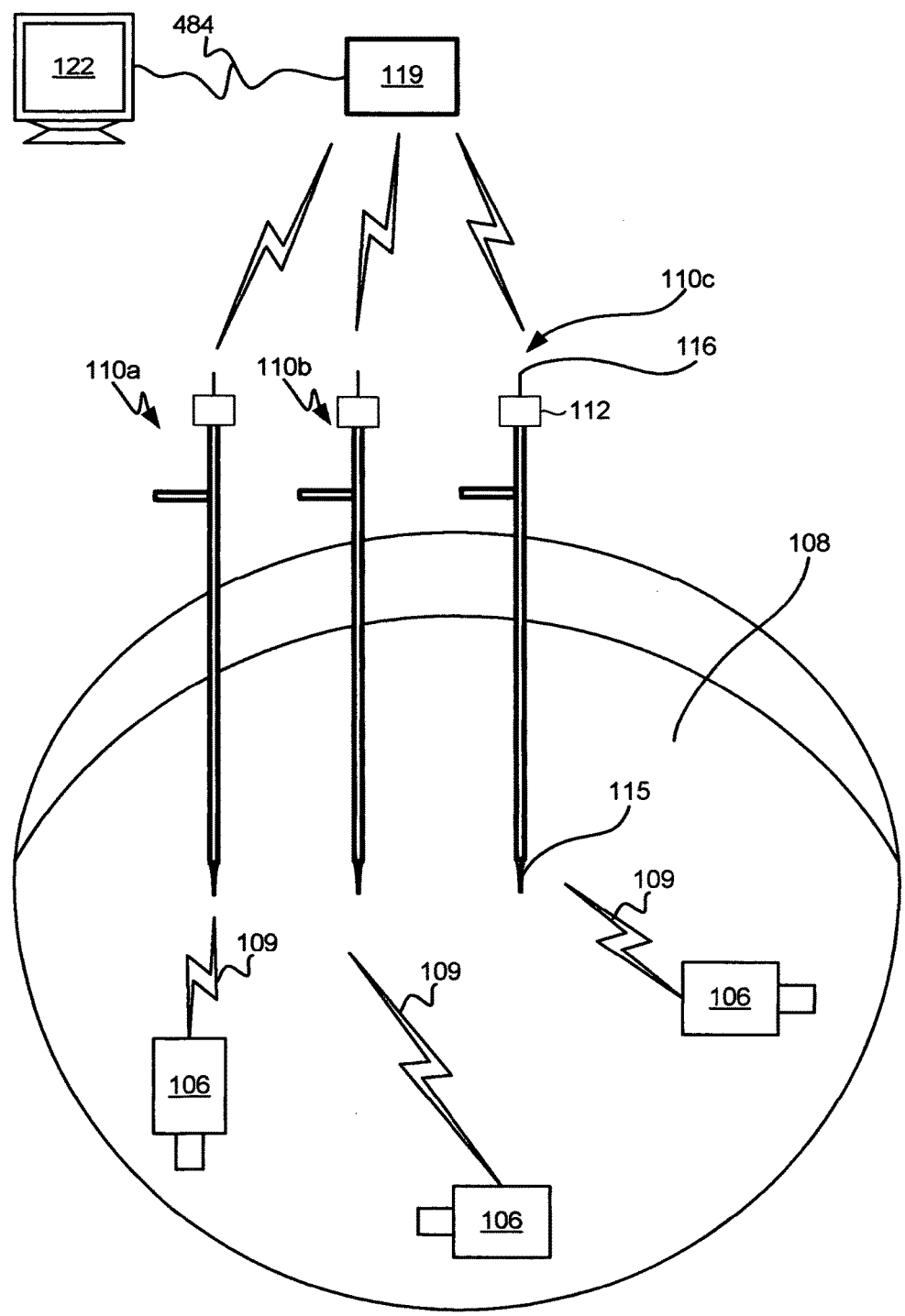
FIG. 15A is a system component diagram of a surgical system including multiple transdermal antennas in one cavity in a surgical procedure according to an embodiment.
Figure 15B:
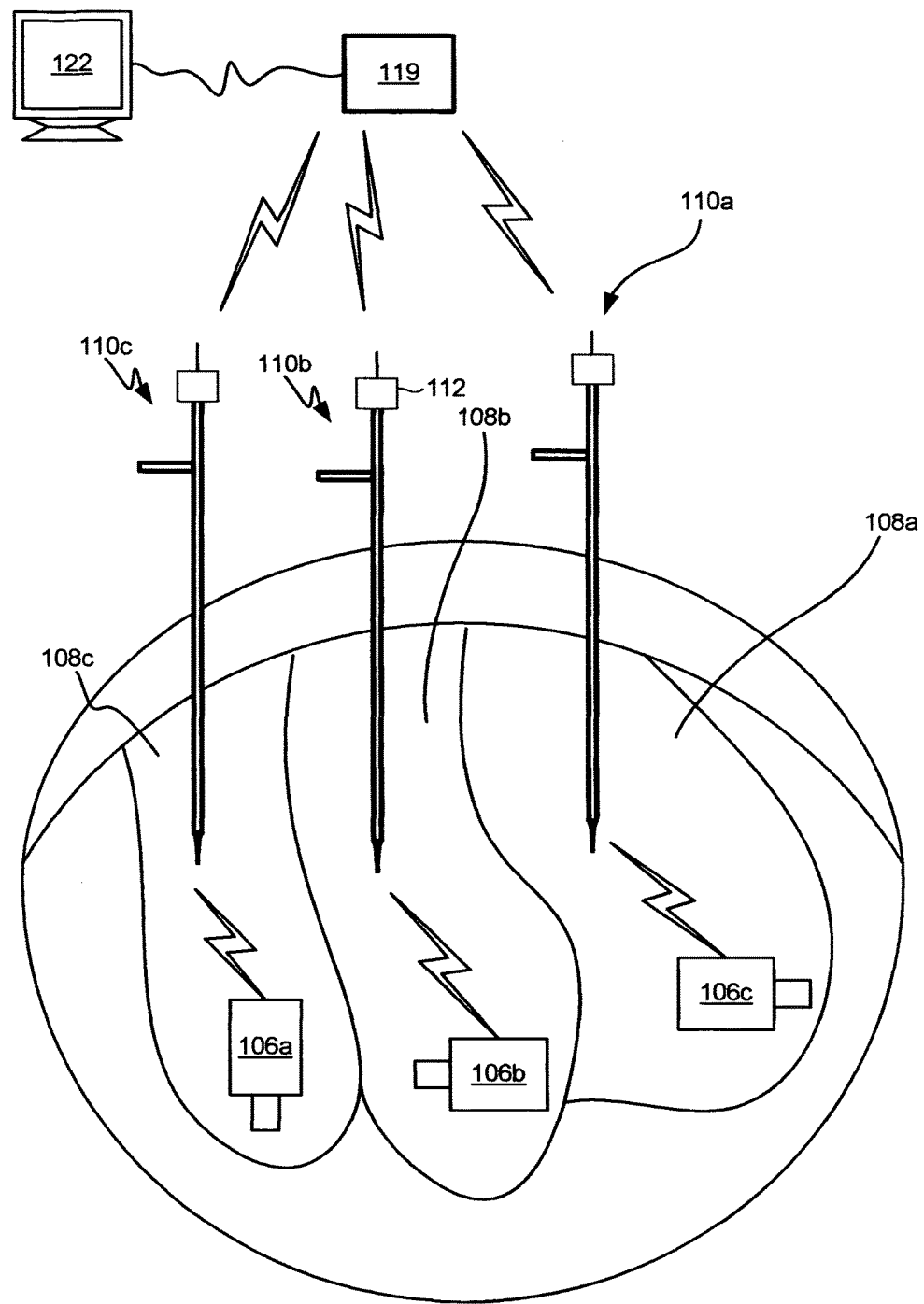
FIG. 15B is a system component diagram of a surgical system including multiple transdermal antennas in multiple cavities according to an embodiment.

The transdermal antenna 110 of the various embodiments may be inserted into the body in a variety of arrangements. As illustrated in FIG. 1, a single transdermal antenna 110 may be used. FIGS. 15A and 15B illustrate two alternative arrangements in which multiple transdermal antennas 110 are used to relay data transmissions from devices inside of the body 100 to an external receiver device 119. As illustrated in FIG. 15A, multiple transdermal antennas 110*a*, 110*b*, 110*c* may be partially inserted into a single body cavity 108. In such an arrangement, image data transmissions 109 by cameras 106 located in the body cavity 108 may be received by one or more of the inner antennas 115 which each conduct the received signals to transceivers 112 which re-transmit the received signals via outer antennas 116 or conduct the received signals via cables 118 (not shown in FIG. 15A) to an external receiver device 119. The use of multiple transdermal antennas 110 may provide signal gain advantages or enable signals to be conducted by one antenna when another antenna is blocked by tissues.

In a second arrangement illustrated in FIG. 15B, multiple transdermal antennas 110*a*, 110*b*, 110*c* may be inserted into different and separate body cavities 108*a*, 108*b*, 108*c*. For example, a first transdermal antenna 110*a* may be inserted into the abdominal cavity 108*a*, another transdermal antenna 110*b* may be inserted into the pleural cavity 108*b*, and a third transdermal antenna 110*c* may be inserted into the pericardial cavity 108*c*. In each body cavity 108*a*, 108*b*, 108*c* the transdermal antenna 110*a*, 110*b*, 110*c* receives image data transmissions from cameras 106*a*, 106*b*, 106*c* positioned within each cavity 108*a*, 108*b*, 108*c*. Each transdermal antenna 110*a*, 110*b*, 110*c* may conduct the data transmissions from cameras 106*a*, 106*b*, 106*c* from inside of a body cavities 108a, 108b, 108c to an external receiver device 119 via wireless transceivers 112 or wired cables 118 (not shown). The use of multiple transdermal antennas 110a, 110b, 110c in this configuration enables a surgeon to simultaneously review images from cameras placed inside different cavities.

Figure 16:
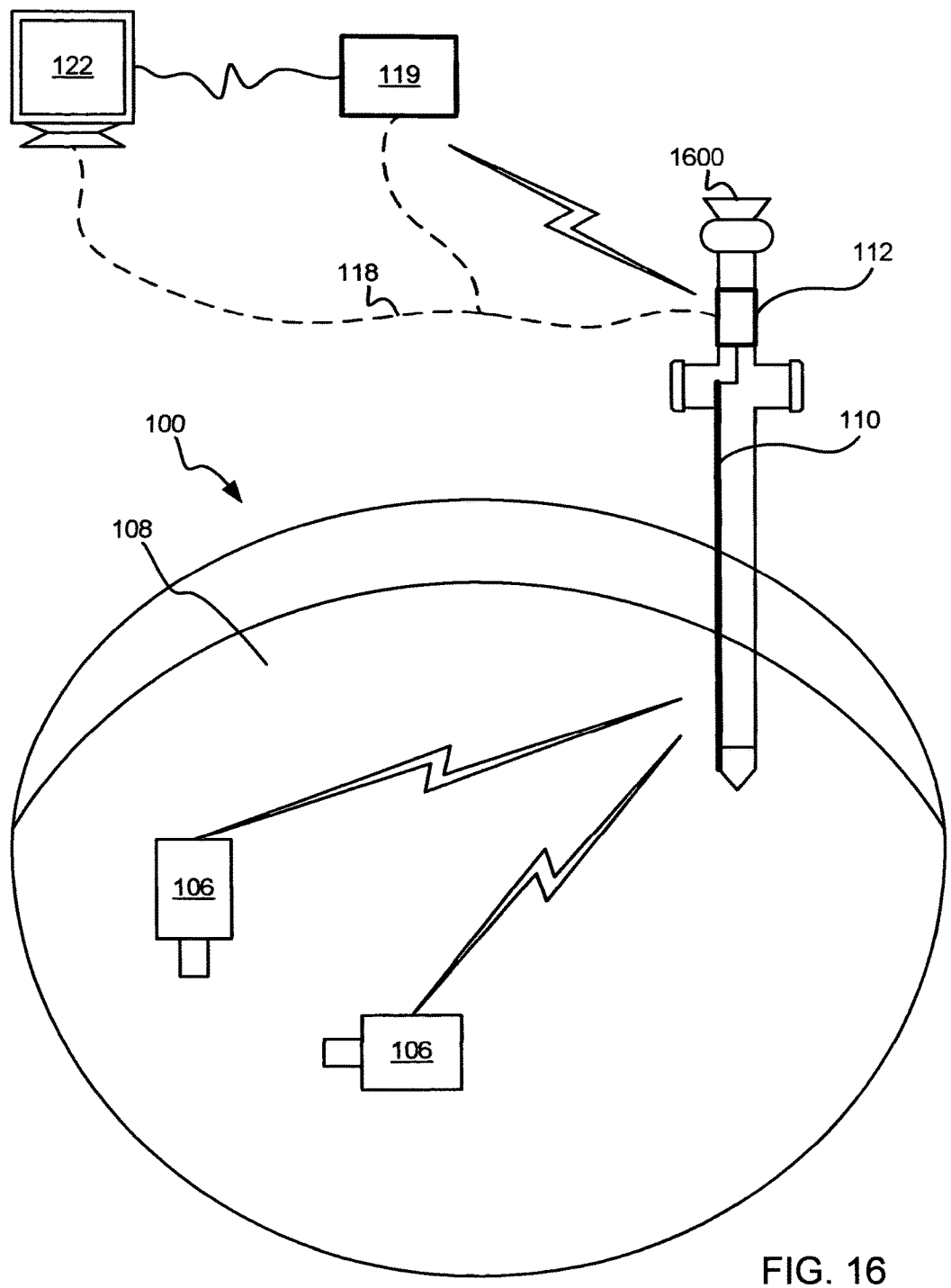
FIG. 16 is a system component diagram of a surgical system including a transdermal antenna within a trocar according to an embodiment.

To reduce the number of instruments that penetrate a patient's body during an operation, the transdermal antenna 110 may be combined with other surgical instruments that must also be inserted into the body 100 anyway. FIG. 16 illustrates an embodiment transdermal antenna 110 attached to or constructed within a trocar 1600. When such a trocar 1600 is partially inserted into a body cavity 108, the integrated transdermal antenna 110 can relay data transmissions from devices positioned within the body 100, such as cameras 106 to external receiver devices 119. The data transmissions received by the transdermal antenna 110 may be conducted to a transceiver 112 which may be directly connected to the trocar 1600. The transceiver 112 may receive the data transmissions and re-transmit the data transmissions wirelessly, or conduct the data transmissions via a wire connection 118, to an external receiver device 119.

FIG. 1 and FIG. 16 illustrate embodiments of a plurality of cameras transmitting from a plurality of locations. The transmissions may be over different carrier frequencies or over the same frequency but different time slots. A wireless network is created for the synchronization, coordination and resource allocation enabling simultaneous transmission of image data from all the cameras.

Figure 17:
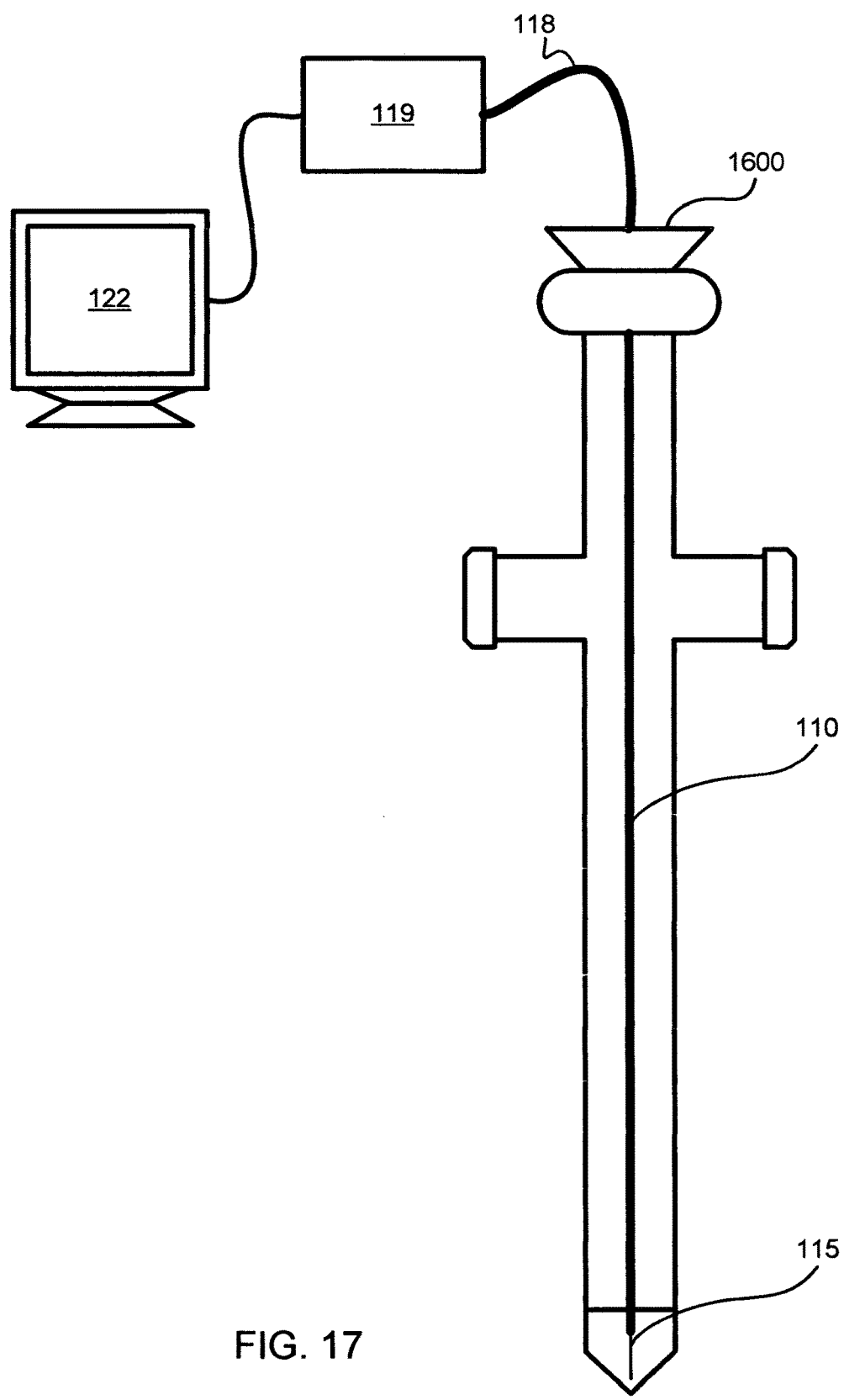
FIG. 17 is a cross sectional view of a trocar including a transdermal antenna and a wire connection to an external receiver device according to an embodiment.
Figure 18:
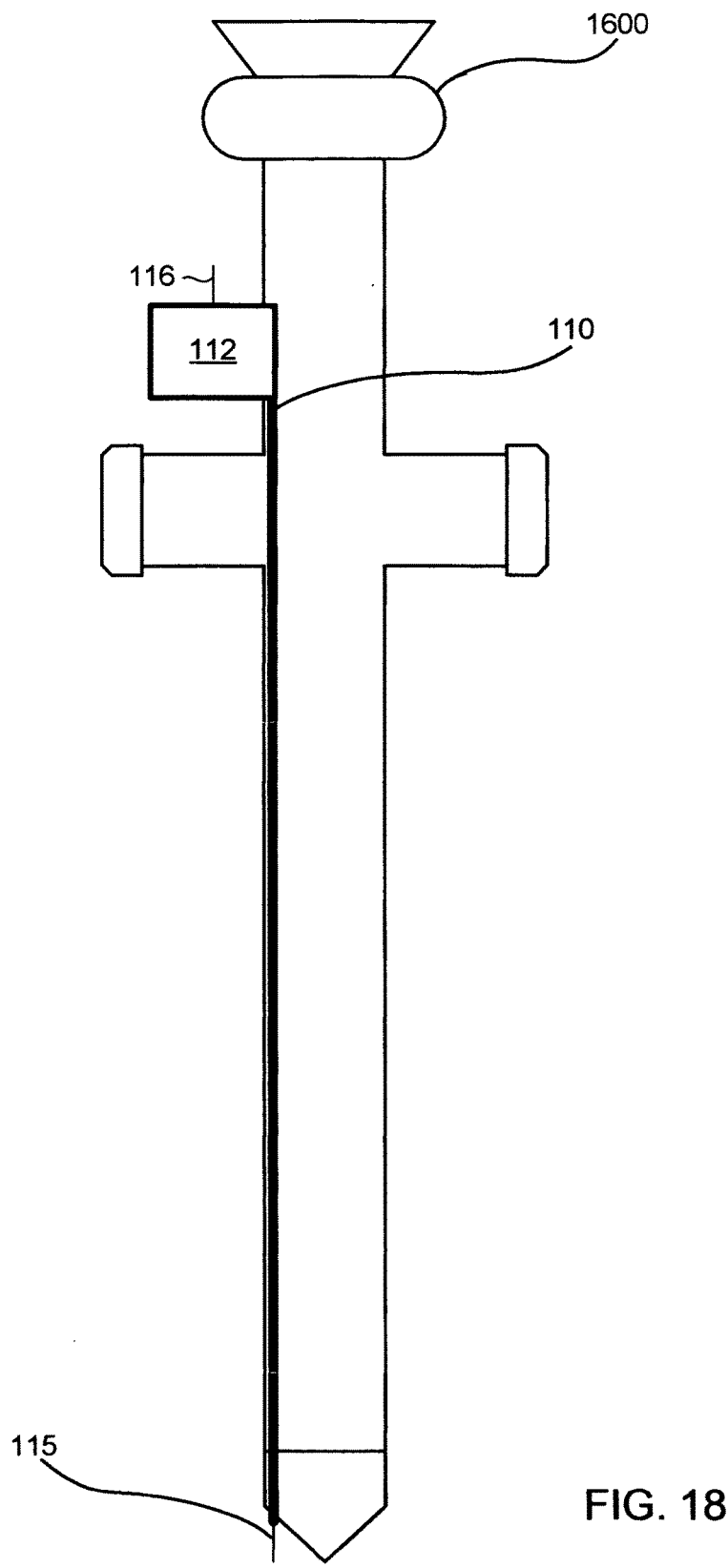
FIG. 18 is a cross sectional view of a trocar including a transdermal antenna according to an embodiment.

FIG. 17 illustrates an embodiment of a transdermal antenna 110 attached to or constructed within a trocar 1600 in which a wire connection 118 connects the transdermal antenna 110 to the external receiver device 119. FIG. 18 illustrates an embodiment transdermal antenna 110 attached to or constructed within a trocar 1600 in which the relay mechanism is a wireless transceiver 112. In this configuration, when the trocar 1600 is inserted into a body cavity 108, data transmissions from devices 106 inside the body cavity 108 received by the inner antenna 115 are conducted to the transceiver 112 for re-transmission via an outer antenna 116.

Figure 19A:
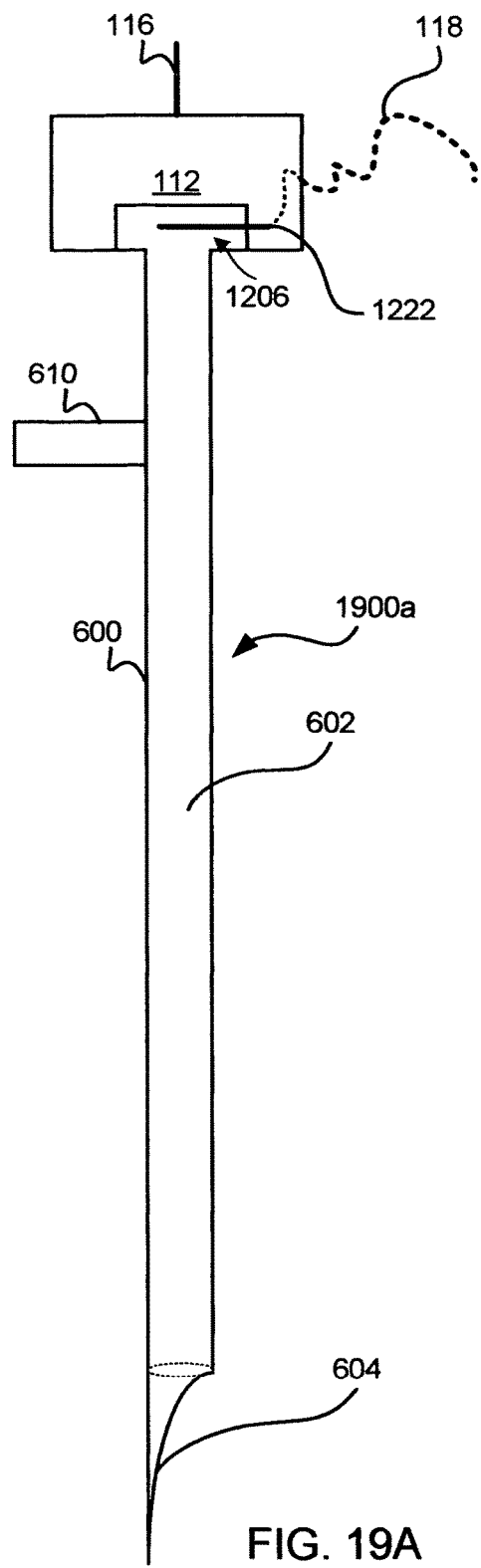
FIGS. 19A-19B are cross sectional views of alternative embodiment transdermal antennas including waveguides.
Figure 19B:
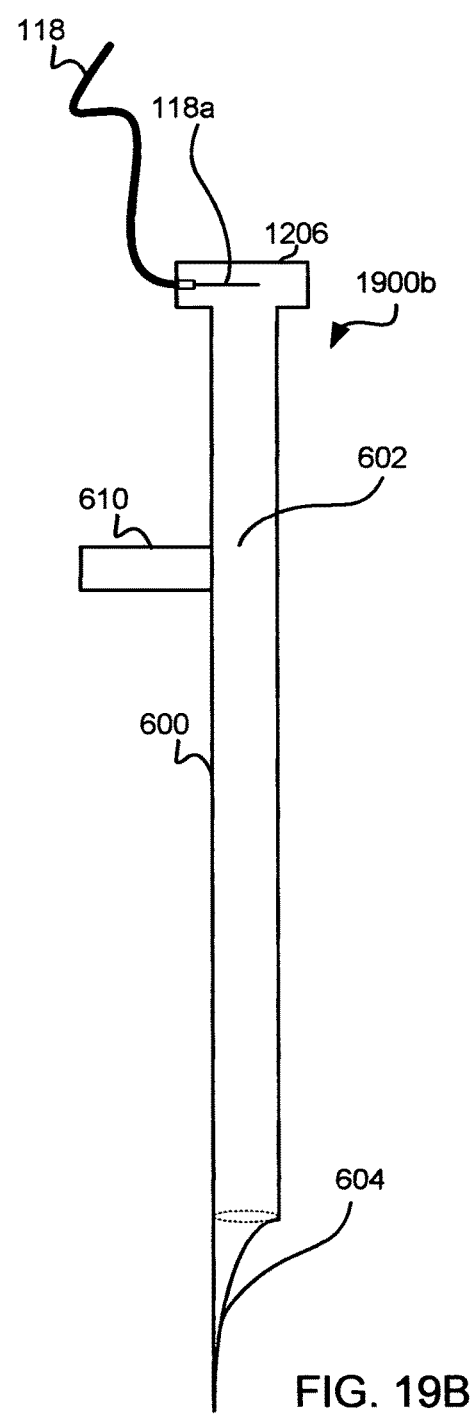

The transdermal antenna 110 embodiment may conduct radio frequency signals received at the internal antenna to a cable or transceiver at its distal end via an internal waveguide 1900. FIGS. 19A and 19b illustrate two example waveguide 1900 configurations that may be used. The waveguide 1900 may include a shaft 600, a lumen 602, a wave collecting tip 604 and a stopper 610. The shaft 600 may be made from metal, such as gold plated stainless steel or aluminum, to allow transmission of radio frequency energy through the shaft 600 from the proximal portion of the shaft 600 to its distal end. For transmitting radio frequency signals in the 60 GHz frequency range, the interior of the lumen 602 may be approximately 3 mm in diameter. The lumen 602 may be hollow or filled with a dielectric material to prevent other non-dielectric substances, such as human tissue, from entering the lumen 602. The wave collecting tip 604 located on the proximal end of the shaft 600 may be used to receive data transmissions from devices located inside of a body cavity 108.

The wave collecting tip 604 may be formed in a variety of configurations. For example, as illustrated, the wave collecting tip 604 may be formed by tapering the proximal end of the shaft 600 to allow the formation of a sharp point at the proximal end of the wave collecting tip 604. A sharp point at the proximal end of the wave collecting tip 604 may allow surgeons to pierce skin, fat and muscle with ease when inserting the waveguide 1900 into a body cavity 108. A stopper 610 may prevent the waveguide 1900 from inadvertently falling into the patient's body 100.

The waveguide 1900 may be formed in a variety of configurations. As shown in FIG. 19A, the waveguide 1900a may couple to a waveguide-to-coax-transition 1206 which receives and conducts signals to a transceiver 112 which can re-transmit data transmissions via an outer antenna 116. As described above, the waveguide-to-coax-transition 1206 typically will include a probe 1222 which extends into the waveguide 1900a to receive radio frequency energy. Optionally, the transceiver 112 may be connected to an external receiver device 119 via an external coaxial cable 118.

In a further configuration illustrated in FIG. 19B, the waveguide 1900b may terminate in a waveguide-to-coax-transition 1206 that is connected to a coaxial cable 118. For example, the waveguide-to-coax-transition 1206 may be formed by extending the central conductor 118a of the coaxial cable 118 into the waveguide 1900b to form a probe that receives radio frequency energy. Data transmissions received by the probe 118a are then conducted to the external receiver device 119 via the coaxial cable 118.

Figure 20:
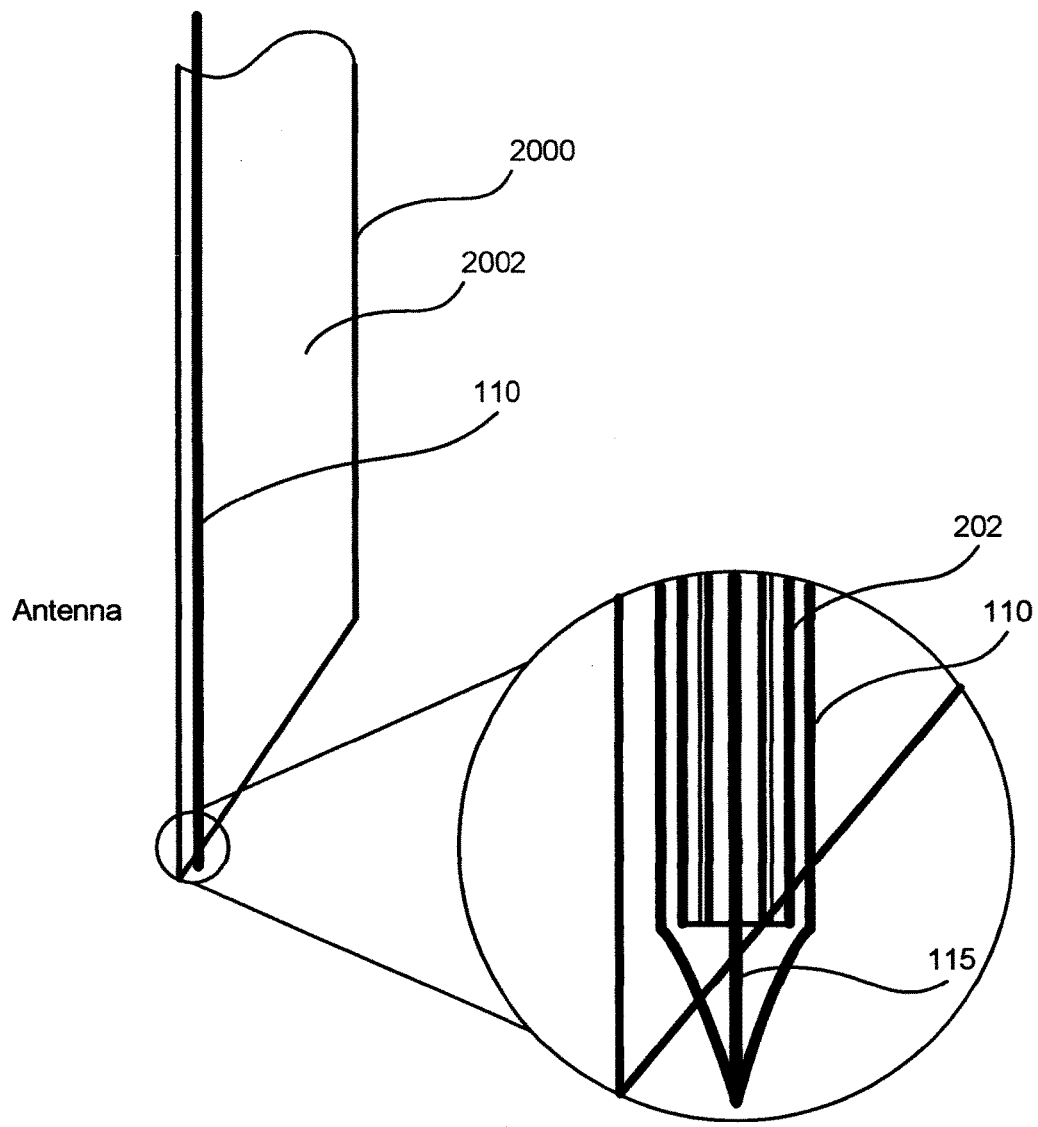
FIG. 20 is a cross sectional view and a detailed view of an inflation needle including a transdermal antenna according to an embodiment.

FIG. 20 illustrates an inflation needle 2000 including a transdermal antenna 110 according to an embodiment. Inflation needles 2000 may be inserted into a patient's body to introduce gases into a body cavity 108. Introducing gases may separate the tissues and create an inflated cavity in which a surgeon can identify anatomical structures and operate. As shown, a transdermal antenna 110 may be configured within an inflation needle 2000 so only a single puncture is required to both inflate the cavity and conduct wireless signals through the dermal layers. The transdermal antenna 110 may be attached to the inflation needle 2000 or be free moving within the lumen of the inflation needle 2002. If the transdermal antenna 110 is attached to the inflation needle 2000, the depth of the transdermal antenna 110 within the body may be adjusted by adjusting the depth of the inflation needle 2000. If the transdermal antenna 110 is freely positioned within the lumen 2002 of the inflation needle 2000, the depth of the transdermal antenna 110 may be adjusted by moving the transdermal antenna 110 inwardly or outwardly with the inflation needle 2000.

For example, the transdermal antenna 110, illustrated in FIG. 20 is a coaxial transdermal antenna 110 positioned freely inside of the inflation needle. Once the inflation needle 2000 is inserted into the body, the surgeon may extend or retract the transdermal antenna 110 within the body cavity 108.

The shaft 200 of the transdermal antenna 110 in the various embodiments may be made of a variety of medically safe materials. Several criteria may be used in selecting a type of material that may be used for constructing the shaft of the transdermal antennas 110. For example, the material used for constructing the transdermal antenna 110 should be non-allergenic. Additionally, the transdermal antennas 110 that may be inserted into a body cavity 108 may require strong materials, such as stainless steel, to withstand the stress of penetrating tissues during surgery. The shaft material may be metal or nonmetal (e.g. plastic). In transdermal antennas 110 comprising waveguides, the shaft material must be conductive metal, such a metal alloy, to allow effective transmission of radio frequency energy.

Different outer antennas 116 may also be used in the various embodiments. For example, the outer antenna 116 may be a monopole, omni-directional or directive (high gain) antenna. A monopole antenna is a type of radio antenna formed by replacing one half of a dipole antenna with a ground plane at right-angles to the remaining half. An omni-directional antenna is an antenna system which radiates power uniformly in one plane with a directive pattern shape in a perpendicular plane. A high gain antenna is an antenna with a focused, narrow radio wave beam width.

Table 1 is an example link budget for the case illustrated in FIG. 5 where the transceiver is directly attached to the distal end. The table includes antenna parameters for an embodiment of transdermal antenna 110.

TABLE 1

| Parameter | | | | Notes |
|---|---|---|---|---|
| Transmit power (including loss to antenna) | Pt | dBm | 0 | |
| Transmit antenna gain | Gt | dBi | 3 | |
| Bit Rate | R | bps | 1.50E+09 | |
| Transimssion distance | d | m | 0.3 | |
| Center frequency | f | GHz | 60 | |
| Wave length | λ | m | 0.005 | (λ = c/f) |
| Free space loss | Lfs | dB | 57.54 | Free space assumption (−20log10(λ/4πd)) |
| Non-LOS margin | | dB | 10 | |
| Needle Loss | | dB | 5 | 15-25 cm needle containing coaxial or waveguide and antenna |
| Total channel loss | L | dB | 72.5 | |
| Receiver antenna gain | Gr | dBi | 3 | |
| Receiver noise figure (including loss from antenna) | NF | dB | 8 | |
| LOS Received signal | Pr | dBm | −51.5 | Pt + Gt − Lfs + Gr |
| Received signal | Pr | dBm | −66.5 | Pt + Gt − L + Gr |
| Required Eb/No | | | 5 | |
| Sensitivity as a function of bit rate and required Eb/No | | | −69.2 | −174 + NF + Eb/No + 10log10(R) |
| Margin as a function of required Eb/No | | dB | 2.7 | |

Figure 21:
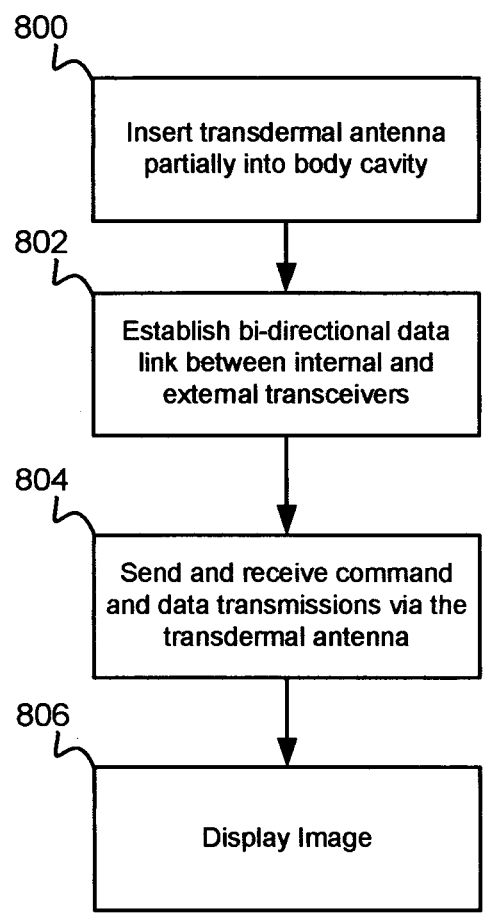
FIG. 21 is a process flow diagram for an embodiment method for treating a patient by using a transdermal antenna.

FIG. 21 illustrates an embodiment method for treating a patient using a transdermal antenna 110 of the various embodiments. In situations where data must be received from devices 106 located within a body, the transdermal antenna 110 may be partially inserted into the body cavity 108, step 800. Positioned in the body cavity 108, the transdermal antenna may conduct radio frequency signals from a device 106 located inside of the body cavity to a receiver device 119 outside of the body. Using this conductive path, the internal devices 106 and external receiver devices 119 can establish a bi-directional data link, step 802. Such a link may be established using known communications protocols. The external receiver devices 119 can receive data transmissions via the transdermal antenna, step 804. The external receiver device 119 can provide data to a display 122 which may receive the data and display an image based on the data received, step 806.

While the foregoing description of the various embodiments refer to radio frequency signals being conveyed from internal wireless devices 106 to external receiver devices 119, the transdermal antenna 110 also conveys control signals from external devices to internal wireless devices 106. Thus, the transdermal antenna 110 of the various embodiments can be used to establish two-way (bi-directional) data and control communication links. Thus, the transdermal antenna 110 can convey control signals to internal wireless devices 106 as well as relay data transmissions from such devices.

The foregoing method descriptions and the process flow diagrams are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the following claims and the principles and novel features disclosed herein.

What is claimed is:

1. A transdermal antenna for transporting data comprised in wireless signals from a cavity inside a mammalian body, to outside the body, the apparatus comprising:
    a trocar comprising a shaft having a first end configured to pierce mammalian tissue and be positioned in the cavity and a second end located outside the cavity when the first end is located in the cavity;
    an internal antenna comprised in the first end of the trocar and configured to receive wireless signals generated inside the cavity;
    an energy conductor coupled to the internal antenna and traverses a length of the trocar within the shaft, such that the energy conductor is operable to transport data comprised in the received signals from the internal antenna to the second end of the trocar; and
    an external antenna or transceiver located at the second end of the trocar and coupled to the energy conductor that receives and transmits the transported data.

2. A transdermal antenna according to claim 1 wherein the shaft comprises a lumen, and the energy conductor comprises the lumen, which functions as a waveguide to transport the wireless signals received by the internal antenna toward the second end outside the body.

3. A transdermal antenna according to claim 2 wherein the first end is an open end.

4. A transdermal antenna according to claim 3 wherein the internal antenna comprises the first end having a size configured to enable radio frequency radiation to enter the shaft.

5. A transdermal antenna according to claim 4 wherein the radio frequency radiation comprises high definition camera signals.

6. A transdermal antenna according to claim 4 wherein the radio frequency radiation has a frequency equal to about 60 GHz.

7. The transdermal antenna according to claim 1 wherein the shaft is made of conductive metal.

8. The transdermal antenna according to claim 1 wherein the interior of the shaft is about 3 mm in diameter.

9. A communication system comprising a source of the wireless signals configured to be inserted into the cavity and a transdermal antenna according to claim 1, wherein the internal antenna of the transdermal antenna is configured to receive wireless signals from the source.

10. A communication system according to claim 9 wherein the source comprises at least one camera configured to be inserted into the cavity.

11. A transdermal antenna for transporting data comprised in wireless signals generated from a cavity inside a mammalian body, to outside the body, the antenna comprising:
- a trocar having a first end configured to pierce mammalian tissue and be positioned inside the cavity and a second end that remains outside the body when the first end is positioned in the cavity;
- an opening located at the first end of the trocar and configured to receive the wireless signals;
- a lumen of the trocar configured to function as a waveguide that transports the wireless signals from the first end of the trocar to the second end of the trocar; and
- an external antenna or transceiver located at the second end of the trocar and coupled to the waveguide.

\* \* \* \* \*